(12) United States Patent
Gangjee

(10) Patent No.: US 10,858,361 B2
(45) Date of Patent: Dec. 8, 2020

(54) PYRAZOLO[4,3-D]PYRIMIDINES AS ANTITUMOR AGENTS

(71) Applicant: Duquesne University of the Holy Spirit, Pittsburgh, PA (US)

(72) Inventor: Aleem Gangjee, Allison Park, PA (US)

(73) Assignee: Duquesne University of the Holy Spirit, Pittsburgh, PA (US)

(*) Notice: Subject to any disclaimer, the term of this patent is extended or adjusted under 35 U.S.C. 154(b) by 0 days.

(21) Appl. No.: 15/929,363

(22) Filed: Apr. 28, 2020

(65) Prior Publication Data

US 2020/0255431 A1      Aug. 13, 2020

Related U.S. Application Data

(62) Division of application No. 16/294,372, filed on Mar. 6, 2019.

(60) Provisional application No. 62/719,259, filed on Aug. 17, 2018, provisional application No. 62/639,654, filed on Mar. 7, 2018.

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC ................................ C07D 487/04; A61P 35/00
See application file for complete search history.

(56) References Cited

U.S. PATENT DOCUMENTS 9,802,937 B2    10/2017   Thormann et al.
2005/0085472 A1  4/2005   Tanaka et al.

FOREIGN PATENT DOCUMENTS

WO        2016210330       12/2016
WO     WO 2016/210330   *  12/2016   ............ C07D 239/70

OTHER PUBLICATIONS

Carlson, R., New Tubulin Targeting Agents Currently in Clinical Development, Expert Opin. Investig. Drugs, 2008, pp. 707-722, vol. 17(5), Informa UK Ltd.
Kavallaris, M., Microtubules and Resistance to Tubulin-Binding Agents, Nature Reviews, 2010, pp. 1-12, vol. 10, Macmillan Publishers Limited.
Gangjee, A., et al., Abstract 4857: Design and Biological Evaluation of Substituted Pyrrolo[3,2-d]pyrimidines as Dual Acting RTK and Microtubule Targeting Agents, ResearchGate, 2016, pp. 1-4, vol. 76, American Association for Cancer Research.
Prota, A., et al., The Novel Microtubule-Destabilizing Drug BAL27862 Binds to the Colchicine Site of Tubulin with Distinct Effects on Microtubule Organization, J. Mol. Biol., 2014, pp. 1848-1860, vol. 426, Elsevier Ltd.
Teichert, A., et al., One-Pot Homolytic Aromatic Substitutions/ HWE Olefinations under Microwave Conditions for the Formation of a Small Oxindole Library, Organic Letters, 2004, pp. 3477-3480, vol. 6, American Chemical Society.
Stengel, C., et al., Class III β-tubulin Expression and In Vitro Resistance to Microtubule Targeting Agents, British Journal of Cancer, 2010, pp. 316-324, vol. 102(2), Cancer Research UK.
Jordan, M., et al., Microtubules as a Target for Anticancer Drugs, Nature Reviews, 2004, pp. 253-265, vol. 4, www.nature.com.
Gangjee, A., et al., Novel Water Soluble, Substituted Pyrrolo[3,2-d]pyrimidines: Design, Synthesis and Biological Evaluation as Antitubulin Antitumor Agents, Pharm Res., 2012, pp. 3033-3039, vol. 29(11), National Institutes of Health Public Access Author Manuscript.
Dumontet, C., et al., Microtubule-Binding Agents: A Dynamic Field of Cancer Therapeutics, Nature Reviews, 2010, pp. 790-803, vol. 9, Macmillan Publishers Limited.
Tommasi, S., et al., Cytoskeleton and Paclitaxel Sensitivity in Breast Cancer. The Role of β-tubulins, Int. J. Cancer, 2007, pp. 2078-2085, vol. 120, Wiley-Liss, Inc.
Prota, A., et al., Structural Basis of Microtubule Stabilization by Laulimalide and Peloruside A, Angew. Chem. Int. Ed., 2014, pp. 1621-1625, vol. 53, Wiley-VCH Verlag GmbH & Co. KGaA.
Ferrandina, G., et al., Class III β-Tubulin Overexpression Is a Marker of Poor Clinical Outcome in Advanced Ovarian Cancer Patients, Clinical Cancer Research, 2006, pp. 2774-2779, vol. 12(9), American Association for Cancer Research.
Prota, A., et al., A New Tubulin-Binding Site and Pharmacophore for Microtubule-Destabilizing Anticancer Drugs, PNAS, 2014, pp. 13817-13821, vol. 111, Sep. 23, 2014.

(Continued)

*Primary Examiner* — Erich A Leeser
(74) *Attorney, Agent, or Firm* — Buchanan Ingersoll & Rooney PC; Craig G. Cochenour, Esq.

(57) ABSTRACT

A compound of Formula II, or optionally a salt or a hydrate of the compound of Formula II is provided:

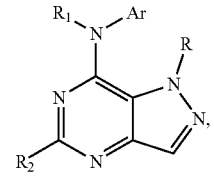

II wherein $R_1$ is selected from the group consisting of a hydrogen, an alkyl group having from one to six carbon atoms, an aryl group, and a heteroaryl group; $R_2$ is selected from the group consisting of an alkyl group having from one to six carbon atoms, a hydrogen, a $NR^aR^b$ group wherein $R^a$ is either a hydrogen or an alkyl group having from one to six carbon atoms and $R^b$ is either a hydrogen or an alkyl group having from one to six carbon atoms, an aryl group, a heteroaryl group, and a halogen; R is an alkyl group having from one to six carbon atoms; and Ar is selected from the group consisting of an alkyl group having from one to six carbon atoms, a substituted aryl, and a substituted heteroaryl.

9 Claims, 7 Drawing Sheets

(56) References Cited

OTHER PUBLICATIONS

Chiou, J.-F., et al., Comparing the Relationship of Taxol-Based Chemotherapy Response with P-glycoprotein and Lung Resistance-Related Protein Expression in Non-Small Cell Lung Cancer, Lung, 2003, pp. 267-273, vol. 181, Springer-Verlag.

Sève, P., et al., Expression of Class III β-Tubulin Is Predictive of Patient Outcome in Patients with Non-Small Cell Lung Cancer Receiving Vinorelbine-Based Chemotherapy, Clinical Cancer Research, 2005, pp. 5481-5486, vol. 11(15), American Association for Cancer Research.

Regiec, A., et al., Methylation of 4-Nitro-3(5)-Pyrazolecarboxylic Acid, Tetrahedron Letters, 2009, pp. 2624-2627, vol. 50, Elsevier Ltd.

Ling, V., Multidrug Resistance: Molecular Mechanisms and Clinical Relevance, Cancer Chemother Pharmacol, 1997, pp. S3-S8, vol. 40, Springer-Verlag.

International Search Report and Written Opinion for PCT/2019/020992 filed Mar. 6, 2019, dated Jul. 3, 2019.

\* cited by examiner

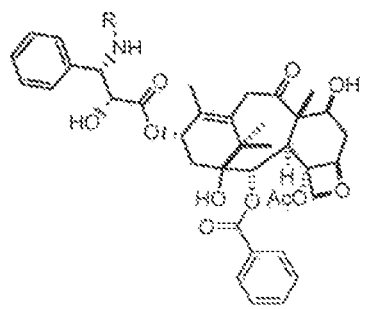
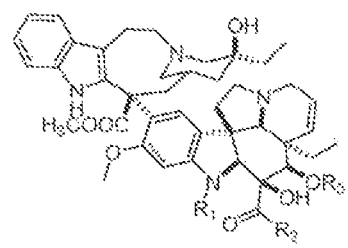
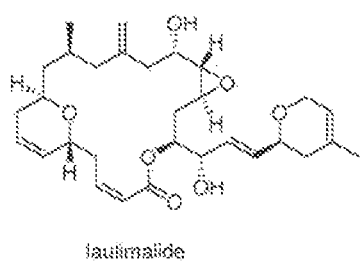
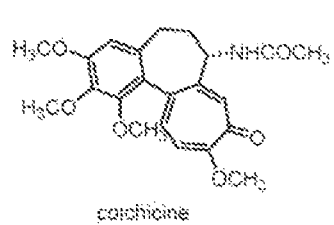
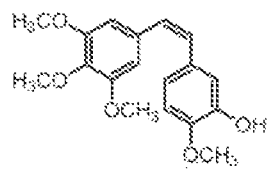
Fig. 1

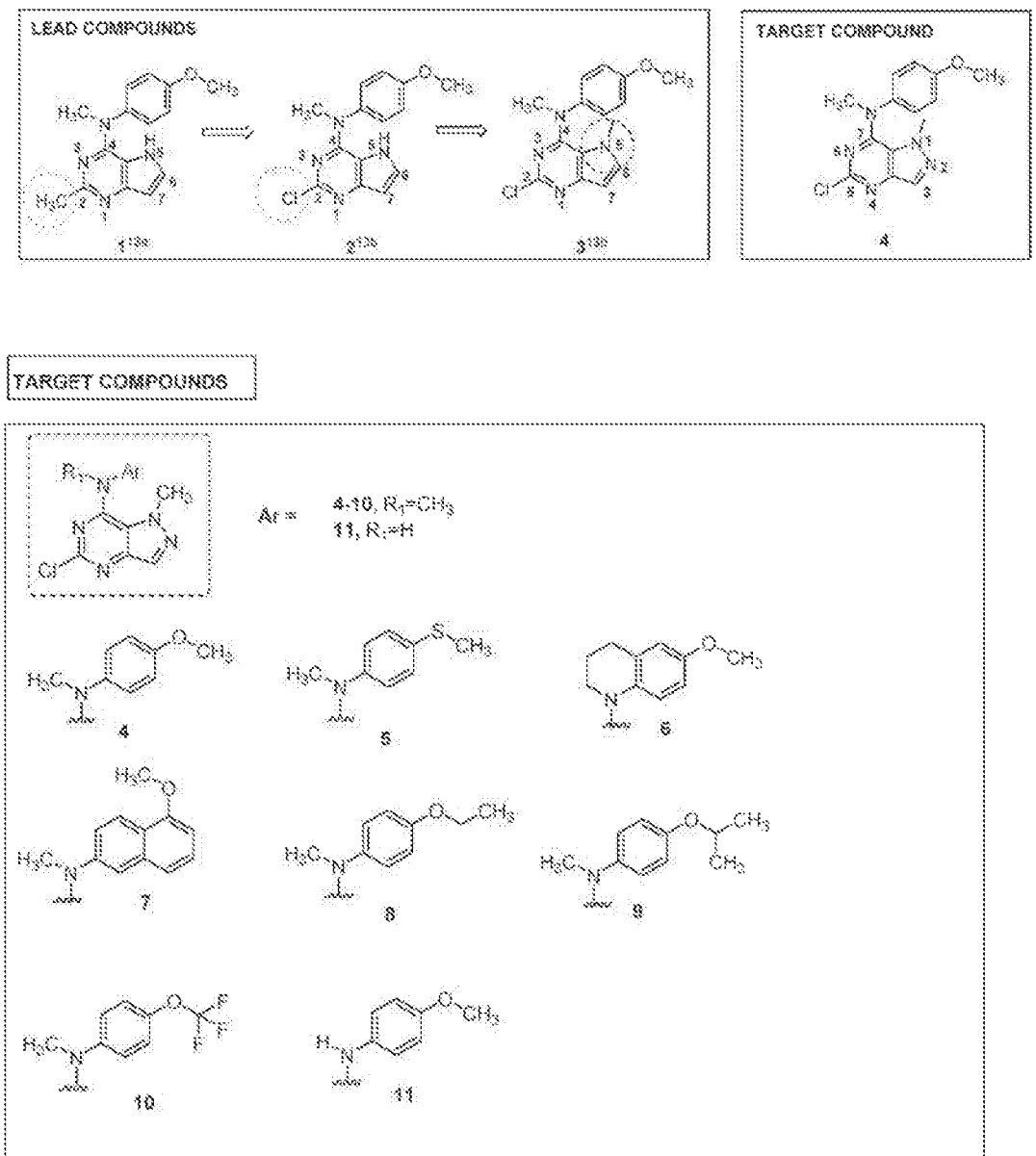
Fig. 2: Structures of Lead compounds and Target compounds

In Vivo activities:

FI/AG 177-359 (Compound 6d1) TUBB3 tumor orthotopic xenograft growth data

Fig. 6 NCI datas of Compound 6d1:

PYRAZOLO[4,3-D]PYRIMIDINES AS ANTITUMOR AGENTS

CROSS-REFERENCE TO RELATED APPLICATIONS

This non-provisional patent application is a divisional patent application of and claims the benefit of co-pending U.S. patent application Ser. No. 16/294,372, filed on Mar. 6, 2019, which claims the benefit of U.S. Provisional Patent Application Ser. No. 62/639,654, filed on Mar. 7, 2018, and to U.S. Provisional Patent Application Ser. No. 62/719,259, filed on Aug. 17, 2018. The entire contents of U.S. patent application Ser. No. 16/294,372, and U.S. Provisional Patent Application Ser. Nos. 62/639,654 and 62/719,259 are incorporated by reference into this non-provisional patent application as if fully written herein.

STATEMENT REGARDING FEDERALLY SPONSORED RESEARCH

This invention was made with government support under grant numbers RO1CA142868 and RO1A1098458 awarded by the National Institutes of Health. The government has certain rights in the invention.

BACKGROUND OF THE INVENTION

1. Field of the Invention

This invention provides pyrazolo[4,3-d]pyrimidine compounds and pharmaceutical compositions and methods of use and manufacture of the same.

2. Description of the Background Art

Microtubule dynamics is a pivotal factor for controlling cell proliferation. Therefore, suppressing cell proliferation by microtubule targeting agents is an outstanding way of controlling cell division.[1] In eukaryotic cells, tubulin heterodimers polymerize to form microtubules. Microtubule formation is a dynamic process which is tightly controlled by cell. Manipulation of the equilibrium between tubulin and microtubule offers an array of opportunities to control cell division. Discovery of new binding sites in tubulin is an additional impetus for designing microtubule targeting agents.

Microtubule targeting agents are mainly classified as two groups, microtubule-stabilizing agents (MSA) and microtubule-destabilizing agents (MDA).[2] Taxanes belong to the first group which bind to the interior of the microtubule. They are useful against breast, lung, ovarian and prostate carcinomas. Laulimalide and peloruside A also belong to the first group which bind to laulimalide binding site, which is a unique non-taxane site in ß-tubulin.[3] Vinca alkaloids such as vincristine, vinblastine consist of the second group which are microtubule destabilizers. These are β-tubulin binding agents used in leukemias, lymphomas and other cancers. Rhizoxin and maytansine bind to the maytansine binding site in ß-tubulin.[4] Colchicines comprise of a diverse collection of molecules which bind at the β-tubulin at its interface with α-tubulin. These are also microtubule destabilizing agents (MDA). Combretastatin A-4 (CA4) and its phosphorylated analog combretastatin A-4 phosphate (CA4-P) which bind to the colchicine site on tubulin are currently in clinical trials. There are no approved colchicine site binding agents. This demonstrates the importance of developing colchicine site agents as antitumor agents.[5] FIG. 1 shows the chemical structures of known agents.

Mutation in the p53 gene occurs in half of all tumors and microtubule targeting agents are most effective in treating p53 mutant cells.[6] Multidrug resistance (MDR) is a major limitation in cancer chemotherapy, and MDR tumors are particularly resistant to tubulin-binding agents.[7] Overexpression of P-glycoprotein (Pgp) has also been reported in a number of tumor types.[8] Attempts to reverse drug resistance by combining antimitotic agents with inhibitors of drug efflux proteins produced disappointing results.[3] Expression of ß-III tubulin is another clinical mechanism of resistance to tubulin binding agents in multiple tumor types including non-small cell lung,[9] breast[10] and ovarian cancer.[11] Stengel et al.[12] showed that colchicine site binding agents are the most effective agents against β-III tubulin resistance which further demonstrates the importance of developing this class of agents.

SUMMARY OF THE INVENTION

The present invention provides compounds of Formula I, and pharmaceutically acceptable salts and hydrates thereof:

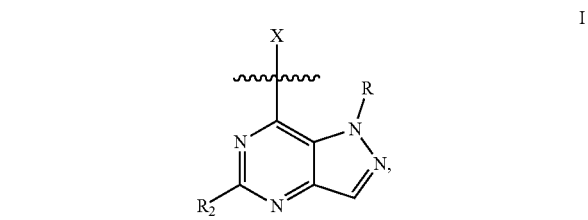

wherein X is selected from the group consisting of:

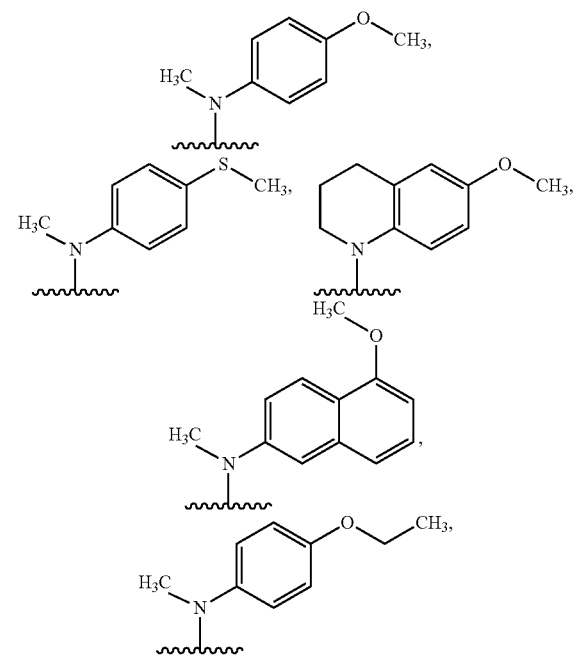

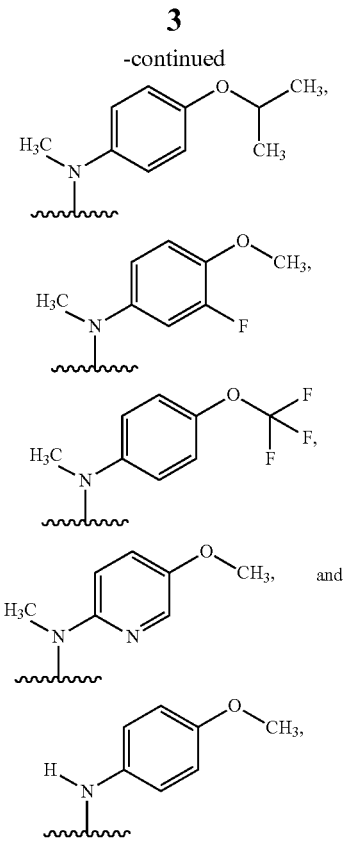

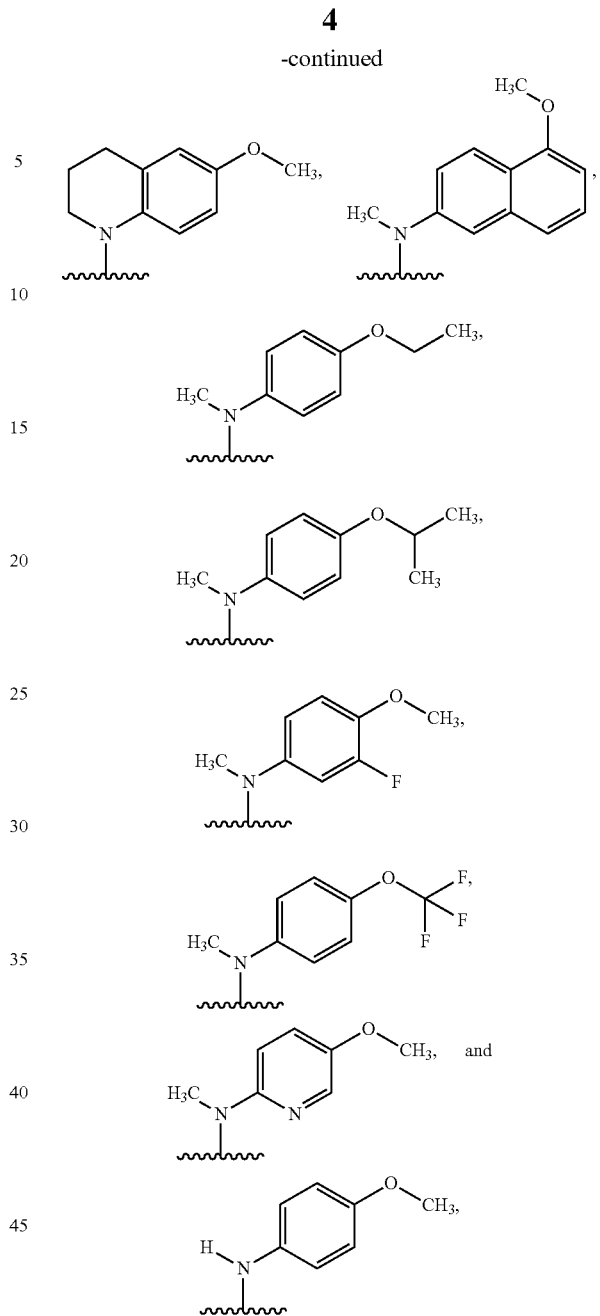

wherein R is an alkyl group having from one to ten carbon atoms, and wherein $R_2$ is a halogen atom. In a preferred embodiment of this invention, the compound of Formula I includes wherein R is a methyl group. In a more preferred embodiment of this invention $R_2$ is a halogen atom that is a chlorine. In a most preferred embodiment of this invention, the compound of Formula I includes wherein R is a methyl group and $R_2$ is a halogen atom that is a chlorine.

Another embodiment of this invention provides a pharmaceutical composition comprising a compound of Formula I, and pharmaceutically acceptable salts and hydrates of the compound of Formula I:

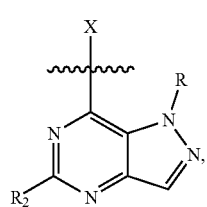

I wherein X is selected from the group consisting of:

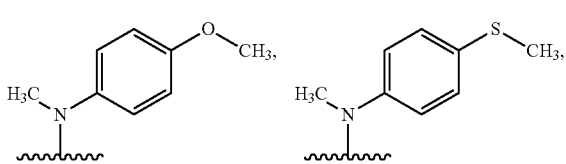

wherein R is an alkyl group having from one to ten carbon atoms, and wherein $R_2$ is a halogen atom. In a preferred embodiment of this invention, the pharmaceutical composition comprises a compound of Formula I, wherein R is a methyl group. In a more preferred embodiment of this invention, the pharmaceutical composition comprises a compound of Formula I, wherein R is an alkyl group having from one to ten carbon atoms and wherein $R_2$ is said halogen atom that is a chlorine. In a most preferred embodiment of this invention, the pharmaceutical composition comprises a compound of Formula I, wherein R is a methyl group and wherein $R_2$ is said halogen atom that is a chlorine.

In another embodiment of this invention, a method of treating a patient having cancer comprises administering to said patient a therapeutically effective amount of a compound of Formula I to said patient:

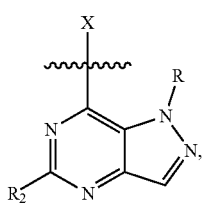

wherein X is selected from the group consisting of:

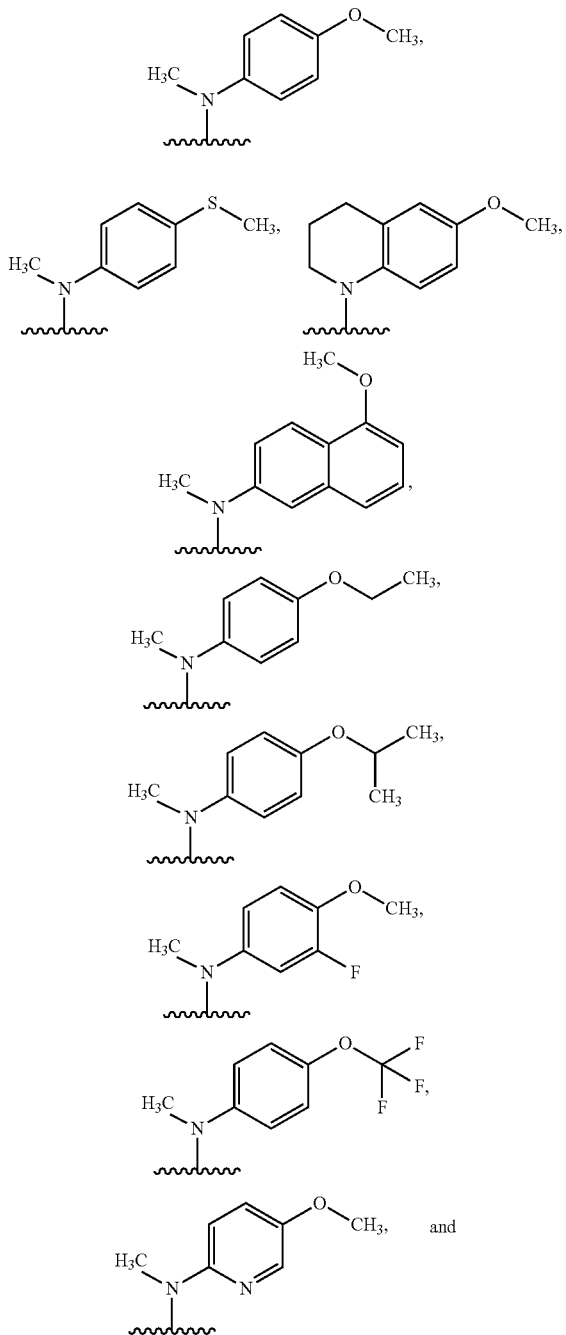

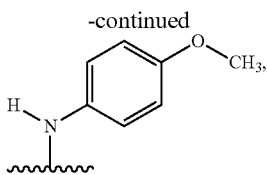

wherein R is an alkyl group having from one to ten carbon atoms, and wherein $R_2$ is a halogen atom. Preferably, this method of treating a patient having cancer includes wherein the compound of Formula I includes wherein R is a methyl group and $R_2$ is said halogen. In a more preferred embodiment of the method of treating a patient having cancer of this invention includes wherein the compound of Formula I includes wherein R is an alkyl group having from one to ten carbon atoms and said halogen atom is a chlorine. In a most preferred embodiment of the method of treating a patient having cancer of this invention includes wherein the compound of Formula I includes wherein R is a methyl group and said halogen atom is a chlorine.

BRIEF SUMMARY OF THE DRAWINGS

FIG. 1 shows the chemical structures of known anti-cancer agents.

FIG. 2 shows the chemical structures of known in the art lead compounds and shows the chemical structures of the target compounds of the present invention.

Figure 6:
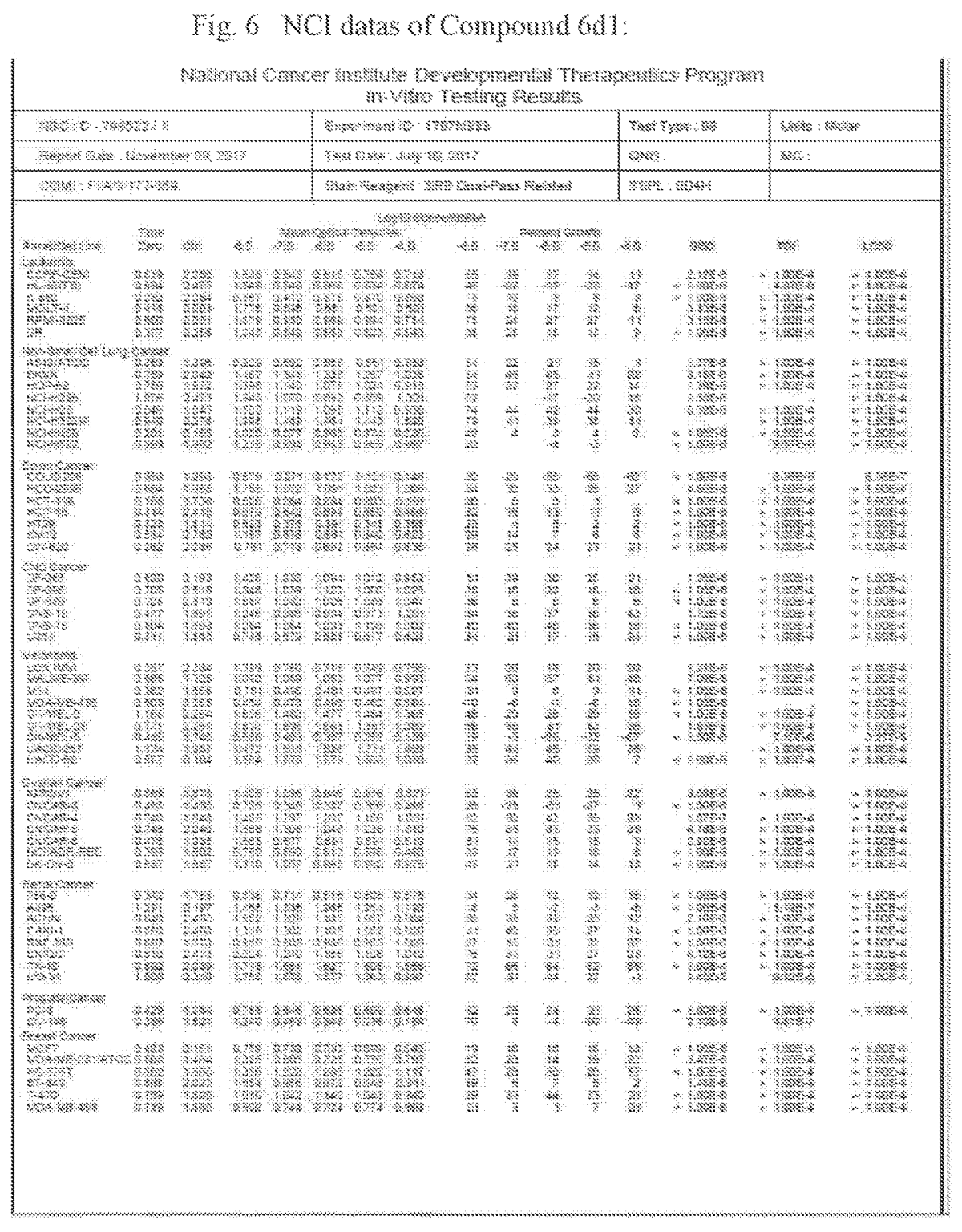

FIG. 6 shows the National Cancer Institute Developmental Therapeutics Programs In-vitro testing results for compound 6d1 of the present invention. Compound 6d1 of the present invention is also identified as "FI/AG 177-359" herein. Compound 6d1 is 5-chloro-N-(4-methoxyphenyl)-N,1-dimethyl-1H-pyrazolo[4,3-d]pyrimidin-7-amine. Compound 6d1 (Part II: Synthesis Scheme I) is also shown as Compound 4 in Part I: Synthesis Scheme 1, all of which are FI/AG 177-359.

DETAILED DESCRIPTION OF THE INVENTION

Figure 3A:
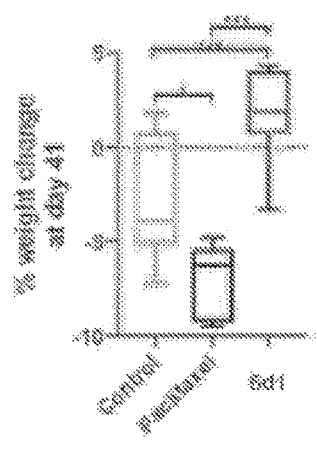
FIG. 3A shows the effects of compound 6d1 of the present invention, namely 5-chloro-N-(4-methoxyphenyl)-N,1-dimethyl-1H-pyrazolo[4,3-d]pyrimidin-7-amine versus paclitaxel (PTX) on animal weight in the MCF-7 TUBB3 (β III tubulin overexpressing) xenograft model.
Figure 3B:
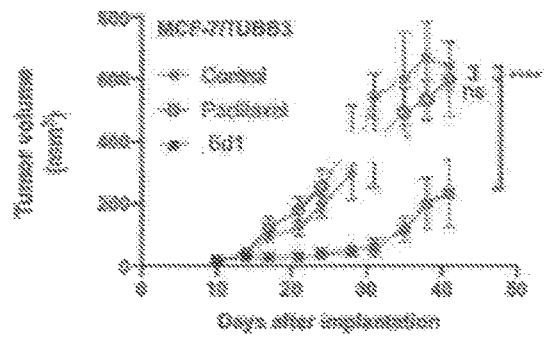
FIG. 3B shows the effects of compound 6d1 of the present invention, namely 5-chloro-N-(4-methoxyphenyl)-N,1-dimethyl-1H-pyrazolo[4,3-d]pyrimidin-7-amine versus paclitaxel on primary tumor growth in the MCF-7 TUBB3 (β III tubulin overexpressing) xenograft model.
Figure 4:
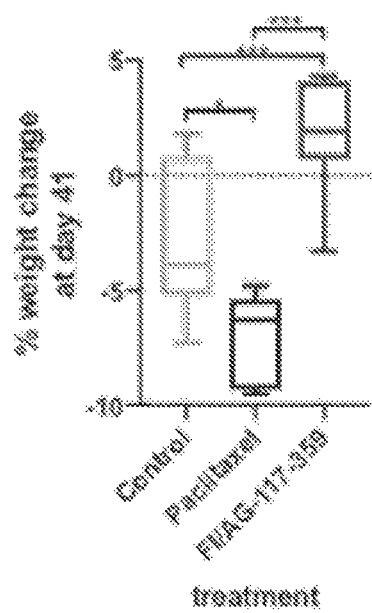
FIG. 4 shows the animal weights (day 41 vs day 0) *=P<0.05; *** P<0.001 (0.0007 for control vs FI/AG 177-359 (i.e. Compound 6d1), 0.0003 for PTX vs FI/AG 177-359).
Figure 5:
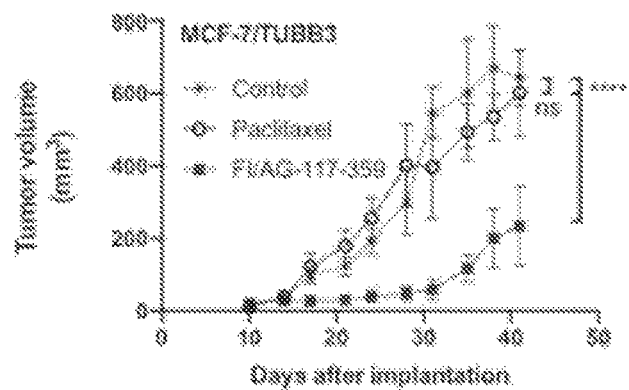
FIG. 5 shows the FI/AG 177-359 compound at its maximal tolerated dose of 30 mg/kg 2× weekly was significantly (P<0.0001) better at reducing MCF-7 TUBB3 (beta III tubulin overexpressing; 1×01exp7 cells/100 uL Matrigel implanted into fat pad #4 of 8 week old athymic female mice) growth than either control/solvent or paclitaxel at its MTD of 10 mg/kg/week. Only the control and paclitaxel mice lost weight at the end. Sample sizes are 7 for control (lost an animal in each group toward the end) and PTX and 8 for compound FI/AG 177-359.
Figure 7:
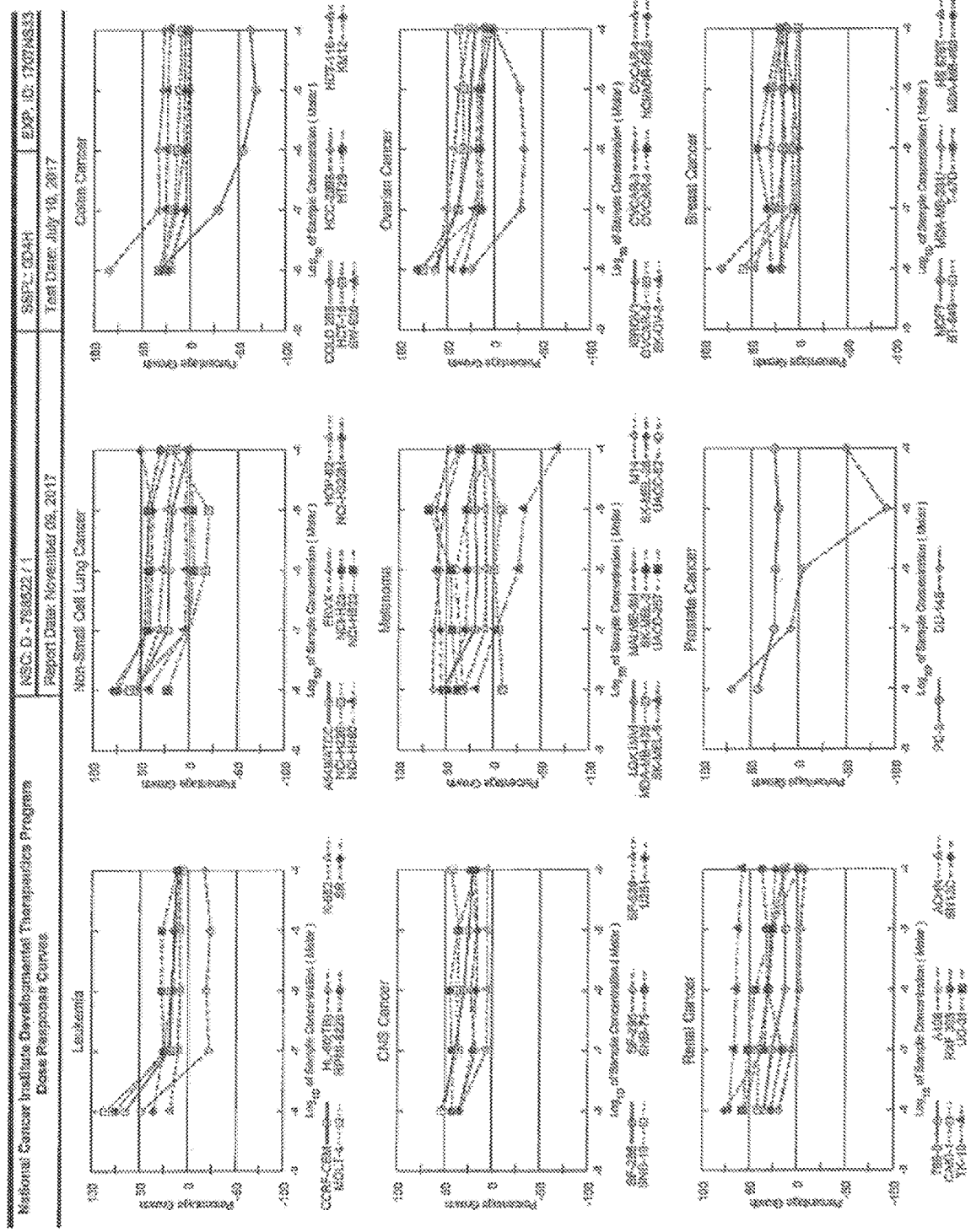
FIG. 7 shows the National Cancer Institute Developmental Therapeutics Program Dose Response Curves for Compound 6d1 (i.e. also identified herein as FI/AG 177-359), for leukemia, non-small cell lung cancer, colon cancer, CNS cancer, melanoma, ovarian cancer, renal cancer, prostate cancer, and breast cancer.

As used herein, the term "patient" refers to a member of the animal kingdom, including but not limited to, human beings.

As used herein, the term "therapeutically effective amount" refers to that amount of a compound required to bring about a desired effect in a patient. The desired effect will vary depending on the illness being treated. For example, the desired effect may be reducing tumor size, destroying cancer cells, preventing metastasis, or reducing symptoms associated with various diseases, including but not limited to cancer. It will be understood by a person of ordinary skill in the art that the "therapeutically effective amount" will vary from patient to patient depending on such factors, for example, but not limited to, the illness being treated, the severity of the illness being treated, and the patient's ability to mount an immune response. The determination of a "therapeutically effective amount" for a given patient is within the skill of one practicing in the art. Generally, a "therapeutically effective amount" is determined by the potency in standard ex vivo cellular systems, and may be followed by pre-clinical and clinical in vivo assessment As used herein, the term "cancer" includes human cancers, for example, but not limited to, leukemia, non-small cell lung cancer, colon cancer, central nervous system cancer, melanoma, ovarian cancer, breast cancer, renal cancer, prostate cancer, and pancreatic cancer. As used herein, the term "having cancer" means that a patient has been diagnosed with cancer.

The present invention provides compounds of Formula I, and pharmaceutically acceptable salts and hydrates of the compounds of Formula I:

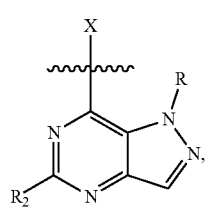

I wherein X is one selected from the group consisting of:

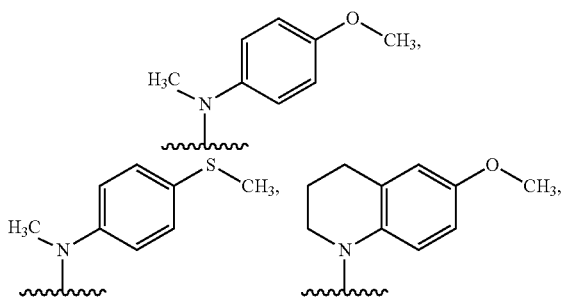

wherein R is an alkyl group having from one to ten carbon atoms, and wherein $R_2$ is a halogen atom. In a preferred embodiment of this invention, the compound of Formula I includes wherein R is a methyl group and wherein $R_2$ is a halogen atom. In a more preferred embodiment of this invention the compound of Formula I includes wherein R is an alkyl group having from one to ten carbon atoms and wherein $R_2$ is a halogen atom that is chlorine. In a most preferred embodiment of this invention, the compound of Formula I includes wherein R is a methyl group and $R_2$ is a chlorine.

In another embodiment of this invention, a pharmaceutical composition is provided comprising the compound of Formula I, or a salt or a hydrate of the compound of Formula I:

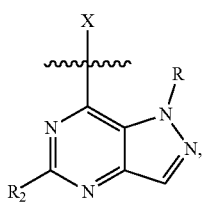

wherein X is selected from the group consisting of:

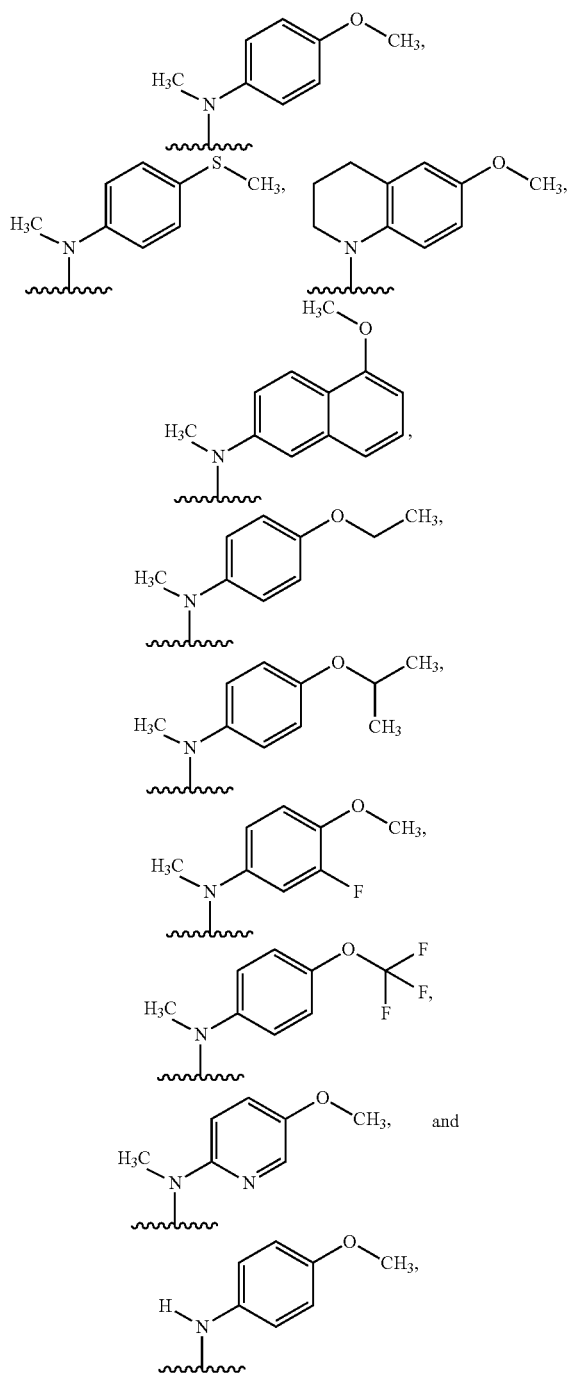

wherein R is an alkyl group having from one to ten carbon atoms, and wherein $R_2$ is a halogen atom. In a preferred embodiment of this invention, the pharmaceutical composition comprises a compound of Formula I, wherein R is a methyl group and $R_2$ is a halogen. In a more preferred embodiment of this invention, the pharmaceutical composition comprises a compound of Formula I including wherein R is an alkyl group having from one to ten carbon atoms and $R_2$ is a halogen atom that is a chlorine. In a most preferred embodiment of this invention, the pharmaceutical composition comprises a compound of Formula I including wherein R is a methyl group and $R_2$ is said halogen that is a chlorine.

Another embodiment of the pharmaceutical composition comprising the compound of Formula I, as described herein, includes a pharmaceutically acceptable carrier.

Another embodiment of this invention provides a compound of Formula II:

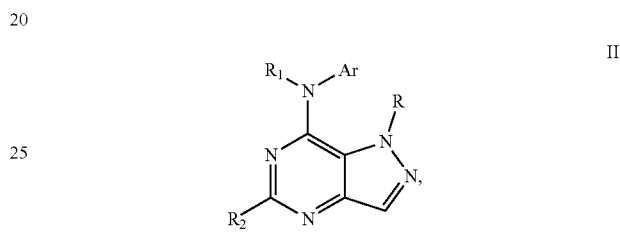

wherein $R_1$ is selected from the group consisting of a hydrogen, an alkyl group having from one to six carbon atoms, an aryl group, and a heteroaryl group; $R_2$ is selected from the group consisting of an alkyl group having from one to six carbon atoms, a hydrogen, a $NR^a R^b$ group wherein $R^a$ is either a hydrogen or an alkyl group having from one to six carbon atoms and $R^b$ is either a hydrogen or an alkyl group having from one to six carbon atoms, an aryl group, a heteroaryl group, and a halogen; R is an alkyl group having from one to six carbon atoms; and Ar is selected from the group consisting of an alkyl group having from one to six carbon atoms, a substituted aryl, and a substituted heteroaryl. In a preferred embodiment of this invention, the compound of Formula II, as described herein, includes wherein $R_2$ is either a methyl group, $NH_2$, or a chlorine. In a more preferable embodiment of this invention, the compound of Formula II, as described herein, is one selected from the group consisting of 5-chloro-N-(4-methoxyphenyl)-N,1-dimethyl-1H-pyrazolo[4,3-d]pyrimidin-7-amine; 5-chloro-N,1-dimethyl-N-(4-(methylthio)phenyl)-1H-pyrazolo[4,3-d]pyrimidin-7-amine; 1-(5-chloro-1-methyl-1H-pyrazolo[4,3-d]pyrimidin-7-yl)-6-methoxy-1,2,3,4-tetrahydroquinoline; 5-chloro-N-(5-methoxynaphthalen-2-yl)-N,1-dimethyl-1H-pyrazolo[4,3-d]pyrimidin-7-amine; 5-chloro-N-(4-ethoxyphenyl)-N,1-dimethyl-1H-pyrazolo[4,3-d]pyrimidin-7-amine; 5-chloro-N-(4-isopropoxyphenyl)-N,1-dimethyl-1H-pyrazolo[4,3-d]pyrimidin-7-amine; 5-chloro-N-(3-fluoro-4-methoxyphenyl)-N,1-dimethyl-1H-pyrazolo[4,3-d]pyrimidin-7-amine; 5-chloro-N,1-dimethyl-N-(4-(trifluoromethoxy)phenyl)-1H-pyrazolo[4,3-d]pyrimidin-7-amine; and 5-chloro-N-(4-methoxyphenyl)-1-methyl-1H-pyrazolo[4,3-d]pyrimidin-7-amine.

As used herein, the term "alkyl" group refers to those alkyl groups having from one to ten carbon atoms, and preferably from one to six carbon atoms, such as for example methyl, ethyl, propyl, butyl, pentyl, hexyl, cyclopropyl, cyclobutyl, cyclohexyl, cyclopropylmethyl or cyclobutylmethyl groups. Alkyl groups sharing one to about six carbon atoms are preferred. These alkyl groups are straight chain, branched chain or cyclic (alicyclic hydrocarbon) arrangements. The carbon atoms of these straight chain, branched chain or cyclic arranged alkyl groups may have one or more substituents for the hydrogens attached to the carbon atoms.

As used herein, the term "heteroalkyl" refers to alkyl chains from one to about 3 atoms where one or more of the carbons has been replaced with nitrogen, oxygen or sulfur, Thus "heteroalkyl" groups will include, for example, $-CH_2-CH_2-NH-$, $-CH_2-S-$, $-S-CH_2-$, $-CH_2-O-$, $-CH_2-CH_2-O-$, $-O-CH_2-$, $-NH-CH_2-CH_2-$, $-NH-CH=CH-$, and other various combinations, as will be apparent to one skilled in the art. The above list is not meant to be exhaustive, and many combinations are contemplated as within the scope of the present invention.

The term "aryl" groups, as used herein, refers to compounds whose molecules have an aromatic ring structure, such as the six-carbon ring of benzene, or multiple rings which are either fused or unfused, such as condensed six-carbon rings of other aromatic derivatives. The term "aryl" is also defined to include diaryl, triaryl and polyaryl groups, which would have two, three or more rings, respectively. Thus, suitable aryl groups would include, for example, phenyl, biphenyl, naphthyl, phenanthrene, anthracene groups and aryl oxyaryl groups. This list is not meant to be exhaustive, and any aryl group, as these terms are defined above and commonly understood in the art, are within the scope of the present invention.

The term "heteroaryl" refers to aromatic ring structures having at least one atom in the ring which is not carbon, such as oxygen, nitrogen or sulfur. "Heteroaryls" as used herein also refers to aromatic ring structures that are part of larger ring structures, such as two or three member ring systems, which may be fused or unfused, in which one of the rings is as described above. Thus, "heteroaryl" refers to ring systems in which one or more rings contain a heteroatom and one or more rings do not. It will be understood that this list is not meant to be exhaustive, and that any heteroaryl group, as these terms are defined above and commonly understood in the art, are within the scope of the present invention. The heteroaryl ring systems may be fused ring systems or unfused. Examples of heteroaryl ring systems include, for example but are not limited to, pyridine, quinoline, isoquinoline, pyrrole, thiophenes, furans, imidazoles, and the like, as well as fused ring structures having rings of different sizes, such as benzofurans, indoles, purines, and the like.

Also included within the scope of the present invention are alicyclic groups, as that term is understood in the art, and heterocyclic groups. As used herein, the term "heterocyclic group" refers to non-aromatic cyclic substituents in which one or more members of the ring is not carbon, and is at least one of an oxygen, sulfur or nitrogen atom, for example.

The terms "alkylaryl" (or "alkaryl") or "alkylheteroaryl" as used herein refer to groups having an alkyl moiety attached to an aryl or heteroaryl ring. The alkyl moiety is preferably a straight, branched or cyclic alkyl group having one to about six carbon atoms. This alkyl moiety may also contain oxygen, nitrogen or sulfur, and therefore may be an alkoxy group. The aryl or heteroaryl moiety of the alkylaryl group is a substituted or unsubstituted aryl or heteroaryl group, as these terms are described above. As used herein, the terms "alkylaryl" or "alkylheteroaryl" will also be used to refer to arylalkyl groups or heteroarylalkyl groups, as those terms are understood in the art, and denotes attachment of such a substituent at either the alkyl or the aryl portion of the group. Thus, for example, a benzyl group would be embraced by the term "alkylaryl".

Any of the cyclic substituents described above, such as the aryl, heteroaryl, alkylaryl, alkylheteroaryl, alicyclic, or heterocyclic groups are optionally substituted with one or more substituents as listed above. In the case of more than one substituent, the substituents are independently selected. "Alkoxy groups" and "alkyl groups" include straight or branched chains having up to about ten members.

As used herein, the term "halogen" refers to chlorine, bromine, iodine and fluorine. "Aryl and heteroaryl groups" are as described above. When a carboxylic acid is a substituent, it will be appreciated that the moiety represents an acid such as benzoic acid.

As used herein, the terms "aroyl" or "heteroaroyl", are generally defined in the art as an aromatic or heteroaromatic compound having a carbonyl moiety.

Other embodiments of the present invention provide pharmaceutically acceptable salts, and hydrates of the compounds of Formula I and Formula II. Preferably, the compounds of the present invention represented by Formula I and Formula II may be made into acid salts that are water soluble. Most preferably, these water soluble salts of Formula I and Formula II may be formulated into an oral dosage forms providing orally administered active antitumor agents. In the past, antimitotic agents have been plagued with water solubility problems, such as for example but not limited to Taxol (Bristol-Myers Squibb Company) and combrestastatin, and a variety of solubilizing agents have been employed to improve their water solubility. The present salts of the compounds having Formula I and Formula II overcome such water solubility problems and are generally completely water soluble.

It is especially advantageous to formulate parenteral compositions in dosage unit form for ease of administration and uniformity of dosage. Dosage unit form as used herein refers to physically discrete units suited as unitary dosages for the patients being treated, each unit containing a predetermined quantity or effective amount of a compound of the present invention to produce the desired effect in association with a pharmaceutical carrier. The specification for the dosage unit forms of the invention are dictated by and directly dependent on the particular compound and the particular effect, or therapeutic response, that is desired to be achieved.

Compounds containing Formula I or Formula II, or pharmaceutically acceptable salts, or hydrates thereof, can be administered to a patient (an animal or human) via various routes including parenterally, orally or intraperitoneally. Parenteral administration includes the following routes that are outside the alimentary canal (digestive tract): intravenous; intramuscular; interstitial, intraarterial; subcutaneous; intraocular; intracranial; intraventricular; intrasynovial; transepithelial, including transdermal, pulmonary via inhalation, ophthalmic, sublingual and buccal; topical, including dermal, ocular, rectal, or nasal inhalation via insufflation or nebulization. Specific modes of administration shall depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered to a patient shall depend on the characteristics of the patient being treated, including for example, but not limited to, the patient's age, weight, health, and types and frequency of concurrent treatment, if any, of any other chemotherapeutic agent(s), all of which is determined by the clinician as one skilled in the art.

Compounds containing Formula I or Formula II, or a salt, or a hydrate thereof, that are orally administered can be enclosed in hard or soft shell gelatin capsules, or compressed into tablets. Compounds also can be incorporated with an excipient and used in the form of ingestible tablets, buccal tablets, troches, capsules, sachets, lozenges, elixirs, suspensions, syrups, wafers and the like. Compounds containing Formula I or Formula II can be in the form of a powder or granule, a solution or suspension in an aqueous liquid or non-aqueous liquid, or in an oil-in-water emulsion.

The tablets, troches, pills, capsules and the like also can contain, for example, a binder, such as gum tragacanth, acacia, corn starch, gelating excipients, such as dicalcium phosphate; a disintegrating agent, such as corn starch, potato starch, alginic acid and the like; a lubricant, such as magnesium stearate; a sweetening agent, such as sucrose, lactose or saccharin; or a flavoring agent. When the dosage unit form is a capsule, it can contain, in addition to the materials described above, a liquid carrier. Various other materials can be present as coatings or to otherwise modify the physical form of the dosage unit. For example, tablets, pills, or capsules can be coated with shellac, sugar or both. A syrup or elixir can contain the active compound, sucrose as a sweetening agent, methyl and propyl-parabens as preservatives, a dye and flavoring. Any material used in preparing any dosage unit form should be pharmaceutically pure and substantially non-toxic. Additionally, the compounds of Formula I or Formula II, and a salt thereof, can be incorporated into sustained-release preparations and formulations.

The compounds of Formula I or Formula II, or a salt, or a hydrate thereof, can be administered to the central nervous system, parenterally or intraperitoneally. Solutions of the compound as a free base or a pharmaceutically acceptable salt can be prepared in water mixed with a suitable surfactant, such as hydroxypropylcellulose. Dispersions also can be prepared in glycerol, liquid polyethylene glycols and mixtures thereof, and in oils. Under ordinary conditions of storage and use, these preparations can contain a preservative and/or antioxidants to prevent the growth of microorganisms or chemical degeneration.

The pharmaceutical forms suitable for injectable use include, without limitation, sterile aqueous solutions or dispersions and sterile powders for the extemporaneous preparation of sterile injectable solutions or dispersions. In all cases, the form must be sterile and must be fluid to the extent that easy syringability exists. It can be stable under the conditions of manufacture and storage and must be preserved against the contaminating action of microorganisms, such as bacteria and fungi.

Compounds of the present invention may be contained within, mixed with, or associated with, a suitable (acceptable) pharmaceutical carrier for administration to a patient according to the particular route of administration desired. Suitable or acceptable pharmaceutical carriers refer to any pharmaceutical carrier that will solubilize the compounds of the present invention and that will not give rise to incompatability problems, and includes any and all solvents, dispersion media, coatings, antibacterial and antifungal agents, isotonic agents, absorption delaying agents, and the like. The use of such suitable or acceptable pharmaceutical carriers is well known by those skilled in the art. Preferred carriers include sterile water, physiologic saline, and five percent dextrose in water. Examples of other suitable or acceptable pharmaceutical carriers include, but are not limited to, ethanol, polyol (such as propylene glycol and liquid polyethylene glycol), suitable mixtures thereof, or vegetable oils. The proper fluidity can be maintained, for example, by the use of a coating, such as lecithin, by the maintenance of the required particle size (in the case of a dispersion) and by the use of surfactants. The prevention of the action of microorganisms can be brought about by various antibacterial and anti-fungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating the compound of Formula I or Formula II in the required amount in the appropriate solvent with various of the other ingredients enumerated above, as required, followed by filtered sterilization. Generally, dispersions are prepared by incorporating the sterilized compound of Formula I or Formula. II of this invention into a sterile vehicle that contains the basic dispersion medium and any of the other ingredients from those enumerated above. In the case of sterile powders for the preparation of sterile injectable solutions, the preferred methods of preparation are vacuum drying and freeze drying.

Pharmaceutical compositions which are suitable for administration to the nose and buccal cavity include, without limitation, self-propelling and spray formulations, such as aerosol, atomizers and nebulizers.

The therapeutic compounds of Formula I and Formula II, or a salt, or a hydrate thereof, can be administered to a patient alone or in combination with pharmaceutically acceptable carriers or as pharmaceutically acceptable salts, the proportion of which is determined by the solubility and chemical nature of the compound, chosen route of administration to the patient and standard pharmaceutical practice.

In another embodiment of this invention, a method of treating a patient having cancer is provided, comprising administering a therapeutically effective amount of a compound of Formula I, or a salt of the compound of Formula I, or a hydrate of a compound of Formula I, to the patient:

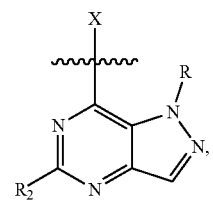

wherein X is selected from the group consisting of:

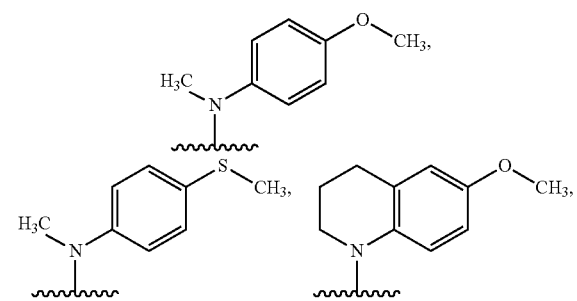

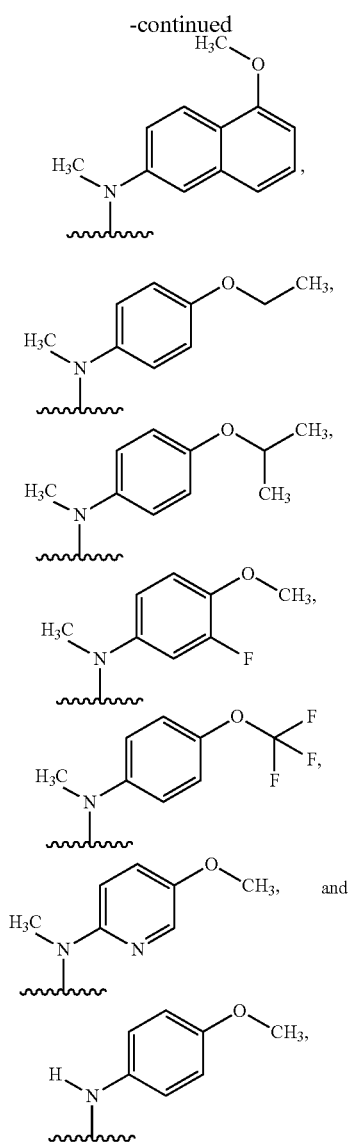

wherein R is an alkyl group having from one to ten carbon atoms, and wherein $R_2$ is a halogen atom. In a preferred embodiment of this invention, the method of treating a patient having cancer includes administering a therapeutically effective amount of the compound of Formula I to the patient wherein the compound of Formula I includes wherein R is a methyl group and $R_2$ is a halogen atom. In a more preferred embodiment of this invention, the method of treating a patient having cancer includes administering to the patient a therapeutically effective amount of the compound of Formula I to the patient wherein R is an alkyl group having from one to ten carbon atoms and $R_2$ is said halogen atom that is a chlorine. In a most preferred embodiment of this invention, the method of treating a patient having cancer includes administering to the patient a therapeutically effective amount of the compound of Formula I to the patient wherein R is a methyl group and $R_2$ is said halogen atom that is a chlorine.

FIG. 2 shows compounds 1, 2, and 3 that are labeled lead compounds that were previously set forth in 2012, by Gangjee et al.[13a, 13b, and 13c, respectively.] Gangjee et al., 2012, reported pyrrolo[3,2-d]pyrimidine known Compound 1 (FIG. 2) that inhibited the binding of radiolabeled colchicine to the tubulin. Known Compound 1 also inhibits the growth of tumor cells with $GI_{50}$ values in the nanomolar range and also circumvents Pgp and βIII-tubulin mediated resistance mechanisms that limit the activity of several microtubule targeting agents.[13a] Known Compound 2 (FIG. 2) with a Cl at the 2-position, was found to be much more active than known Compound 1 (Table 1). The 5-methyl analog known Compound 3 was slightly more active than known Compound 2, indicating that a small group is preferred at the 5-position.[13b] In the present invention, compound 5-methyl-pyrazolo[4,3-d]pyrimidines, compounds of this invention, and those identified herein as compounds 4-11 are presented in FIG. 2. Compounds 4-11 of this invention have a Cl (chlorine) group at the 2-position of pyrazolo[4,3-d]pyrimidine. The present invention explores the SAR (structure activity relationship) of substitution in the anilino ring. While not bound to any particular theory, molecular modeling suggests that, the additional N2-nitrogen at pyrazolo [4,3-d]pyrimidine acts as a hydrogen bond donor (HBD) which is expected to improve binding with the colchicine site. Superimposition of the docked poses of known Compound 3 in the colchicine site of tubulin at the interface of the α-subunit and β-subunit of tubulin; PDB: 4O2B[14] using Maestro 2018[15], were carried out (Docking score=−8.69 Kcal/mol). Superimposition of the docked poses of Compound 4 of this invention in the colchicine site of tubulin at the interface of the α-subunit and β-subunit of tubulin; PDB: 4O2B[14] using Maestro 2018[15], were carried out (Docking score=−9.52 Kcal/mol). The N2-position of pyrazolo[4,3-d] pyrimidine is located 4.40 A° away from Ala317 backbone carbonyl and will be interacted with the enzyme by hydrogen bonding. This specific interaction is absent in known Compound 3.

In the following paragraphs, compounds 4-11 of Part I: Synthesis Scheme I, and compounds 6a-6d and compounds 6d1-6d9 of Part II: Synthesis Scheme, are described as non-limiting examples, of the compounds of the present invention, which are intended to be illustrative only, as numerous modifications and variations therein will be apparent to those skilled in the art.

Part I: Synthesis Scheme I

PART I: Synthesis Scheme I, shows that 4-nitro-1H-pyrazole-3-carboxylic acid (compound 12) was alkylated with methyl iodide in the presence of potassium carbonate in DMF. After flash chromatography on silica gel, two regioisomers, alkyl 1-alkyl-4-nitro-1H-pyrazole-3-carboxylate (compound 13a, 1,3-isomer) and alkyl 1-alkyl-4-nitro-1H-pyrazole-5-carboxylate (compound 13b, 1,5-isomer) were obtained in 26% and 74% yield, respectively. The structures of the isomers (compounds 13a, 13b) were determined by NOESY analysis: a NOESY correlation was observed between H-5 and alkyl protons in compound 13a.[16] The nitro group of compounds 13a and 13b was reduced by hydrogenation in the presence of a catalytic amount of catalytic amount of 10% Pd/C to produce amines compounds 14a and 14b, respectively. Cyclization of compound 14b with urea afforded compound 15. Chlorination of compound 15 with $POCl_3$ and DIPEA in toluene afforded compound 16 in 68% yield. Treatment with appropriate substituted anilines in isopropanol with 1 drop of conc. HCl with compound 16, provided the instant compounds 4-11 of this invention (65-78% yields).

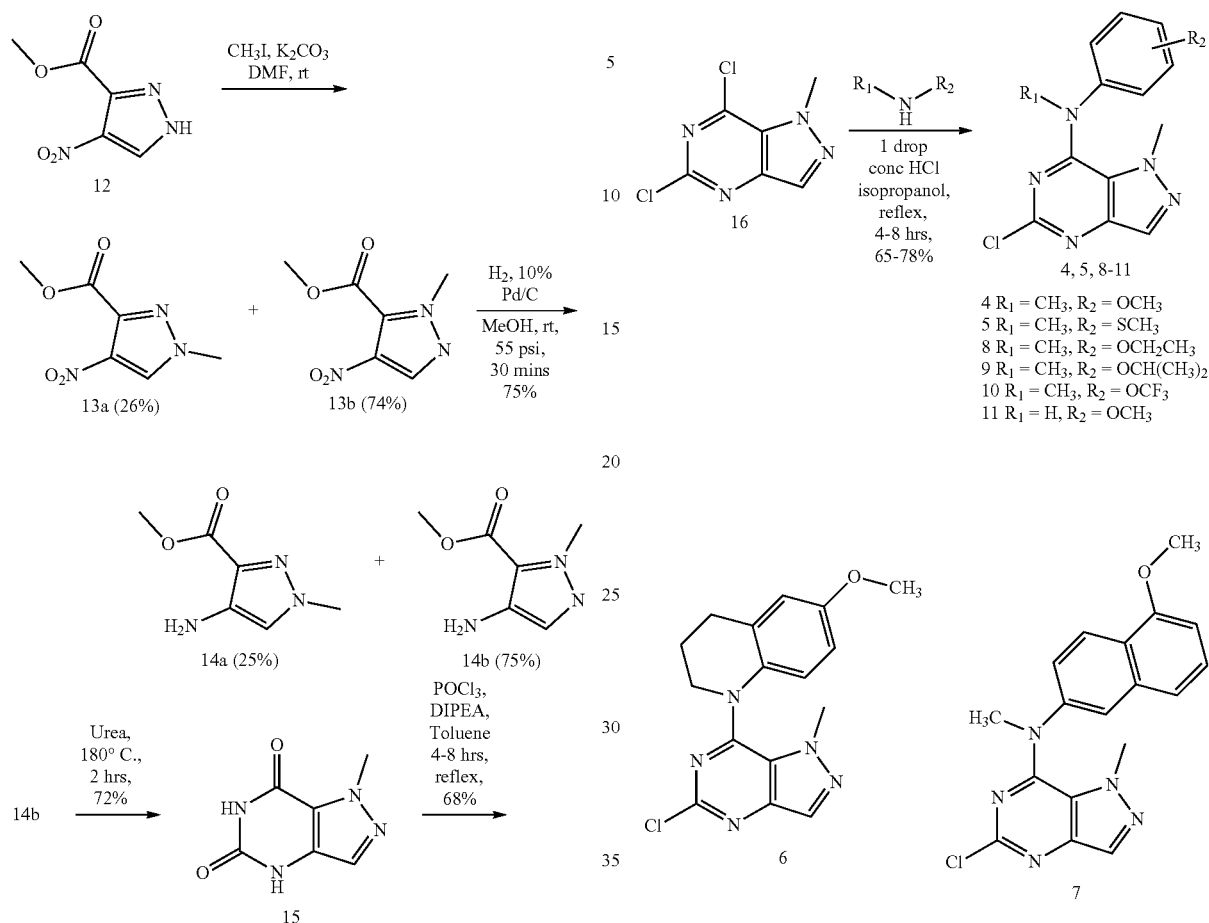

TABLE 1

| | Biological activity | | | | |
|---|---|---|---|---|---|
| | Compound activity in a P-gp overexpressing cell line[a] | | Inhibition of colchicine binding | | |
| | | | 5 μM | 0.5 μM | Inhibition of |
| | OVCAR-8 | NCI/ADR-RES | inhibitor % | inhibitor % | tubulin assembly |
| Compounds | IC$_{50}$ (nM) ± SD | IC$_{50}$ (nM) ± SD | inhibition ± SD | inhibition ± SD | IC$_{50}$ (μM ± SD) |
| Paclitaxel | 7.0 ± 2 | >5,000 | — | — | — |
| CS-A4 | 3.5 ± 0.7 | 2.3 ± 0.4 | 98 ± 0.1 | 80 ± 0.6 | 0.54 ± 0.06 |
| 1 (RP/AG/159-124) | 1000 ± 300 | 700 ± 200 | 95 ± 0.8 | 88 ± 0.7 | 10 ± 0.6 |
| 2 (KS/AG/174-277) | 28 ± 4.0 | 15 ± 4.5 | 96 ± 0.5 | 80 ± 3 | 2.8 ± 0.7 |
| 3 (KS/AG/174-366) | 2.5 ± 0.7 | 1.3 ± 0.4 | 95 ± 0.4 | 97 ± 2.0 | 1.1 ± 0.03 |
| 4 (FI/AG/177-359) | 9.0 ± 0.7 | 5.0 ± 0 | 94 ± 3 | 68 ± 3 | 9.0 ± 0.7 |
| 5 (FI/AG/177-367) | 31 ± 2 | 17 ± 3 | 93 ± 0.5 | 64 ± 2 | 0.82 ± 0.02 |
| 6 (FI/AG/177-353) | 17 ± 2 | 8.0 ± 0.7 | 94 ± 0.4 | 68 ± 2 | 0.42 ± 0.07 |
| 7 (FI/AG/177-456) | 14 ± 3 | 11 ± 0.7 | 91 ± 1 | 66 ± 0.7 | 0.49 ± 0.01 |
| 8 (FI/AG/177-457) | 2.0 ± 1 | 4.0 ± 1 | 99 ± 0.4 | 88 ± 0.8 | 0.42 ± 0.07 |
| 9 (FI/AG/177-458) | 49.0 ± 10 | 44 ± 8.0 | 85 ± 1 | — | 1.1 ± 0.08 |
| 10 (FI/AG/177-463) | 880 ± 40 | 730 ± 100 | 64 ± 5 | — | 2.9 ± 0.2 |
| 11 (FI/AG/177-455) | >5000 | >5000 | 7.1 ± 3 | — | >20 |

Compounds 4-11 of this invention were designed and tested to study the direct effects on tubulin assembly and inhibition of colchicine binding (see Table 1). Except for compounds 9-11, all the compounds at 5 µM inhibited [$^3$H] colchicine binding to the protein, and the extent of inhibition of all the compounds were similar to that obtained with CA-4. Known Compound 2 inhibited tubulin assembly with 3-fold improved activity comparable to the lead known Compound 1. Molecular modeling suggested that (not shown here) 2-Cl of known Compound 2, interacted with the hydrophobic pocket created by Leu248 and Ala 246 amino acids. The 5-Me of lead known Compound 3 is oriented towards the hydrophobic pocket of Ala316, Ala317 and Val315 (not shown). These hydrophobic interactions clearly explained the improved tubulin assembly when comparing known Compound 3 with known Compound 2. Compounds 4-11 of this invention were designed based on the bioisosteric replacement of 2-chloro-N,5-dimethyl-1-pyrrolo[3,2-d]pyrimidine scaffold to 5-chloro-1-methyl-pyrazolo[4,3-d]pyrimidine scaffold. Compounds 4-11 of the present invention inhibited the binding of [$^3$H] colchicine to tubulin by 64-99%, whereas the lead known Compound 1 showed 95% inhibition of [$^3$H]colchicine binding.

Compound 4 of the present invention unexpectedly showed (exhibited) a 2-fold improvement in inhibition of tubulin assembly over known Compound 3. While not bound to any particular theory, the additional N2-nitrogen at pyrazolo[4,3-d]pyrimidine acts as a hydrogen bond donor (HBD) which may explain the unexpected improvement in inhibition of tubulin assembly and binding with the colchicine site. Compound 11 of the present invention, which is the NH-hydrogen on N-4 position of known compound 4 was not active in OVCAR-8 and NCI/ADR-RES cell lines and did not show colchicine inhibition. In compound 11 the sigma bonds ($C_1$—N and N—$C_4$) connecting the phenyl ring and pyrazolo[4,3-d]pyrimidine ring are both freely rotatable, while these bonds are somewhat restricted in known compound 4 where an additional methyl group was introduced on the N-4 position. The $^1$H NMR spectrum of known compound 4 (not set forth herein) shows the 5-CH$_3$ proton in known compound 4 (δ 3.79 ppm) is more shielded than in compound 11 (δ 4.35 ppm, $^1$H NMR spectrum not set forth here). Due to the bulk of the 4-N-methyl group, the conformations of known compound 4 is restricted such that the phenyl ring is conformationally positioned on top of the 5-CH$_3$ (compound 4). This $^1$HNMR study defines the aniline ring orientation, in the N4-CH$_3$ analogs of compound 4, to be oriented on the side of the pyrazolo ring of the pyrazolo [4,3-d]pyrimidine scaffold.

Compound 5 of this invention, where the 4'-methoxy aniline of known compound 4 was substituted with 4'—S-methylaniline resulted in reduced inhibition in tubulin assembly and colchicine binding. This data indicates that bioisosteric replacement of electronegative oxygen of the 4'-OMe group with sulfur in compound 5 is detrimental to tubulin assembly and colchicine binding. Restriction of the N-4 methyl of compound 4 of this invention as a 6-methoxy tetrahydroquinoline ring as compound 6 of this invention and with a 5'-methoxy-2'-N-methyl naphthyl moiety as compound 7 of this invention have parallel inhibition in tubulin assembly and colchicine binding.

Homologation of 4'-OMe (known compound 4) to 4'-OEt (compound 8 of this invention) unexpectedly improves OVCAR-8 cell line activity around 4-fold over known compound 4 and comparable activity of tubulin assembly and colchicine binding inhibition with known compound 4. When bulky side chains —OCH(CH$_3$)$_2$ and —OCF$_3$ (compounds 9 and 10, of this invention, respectively) were introduced at 4'-position OVCAR-8 and NCI/ADR-RES cell line activities were diminished. Tubulin assembly and colchicine inhibition were also decreased. Molecular Modeling revealed that due to the steric clashes of the bulky side chains with Met259 in the colchicine site of the protein (PDB: 402b, figure not shown) the activities are decreased.

Part II: Synthesis Scheme I

N-4 substituted Pyrazolo[4,3-d]pyrimidine compounds as Microtubule Targeting Agents:

Part II: Synthesis Scheme I

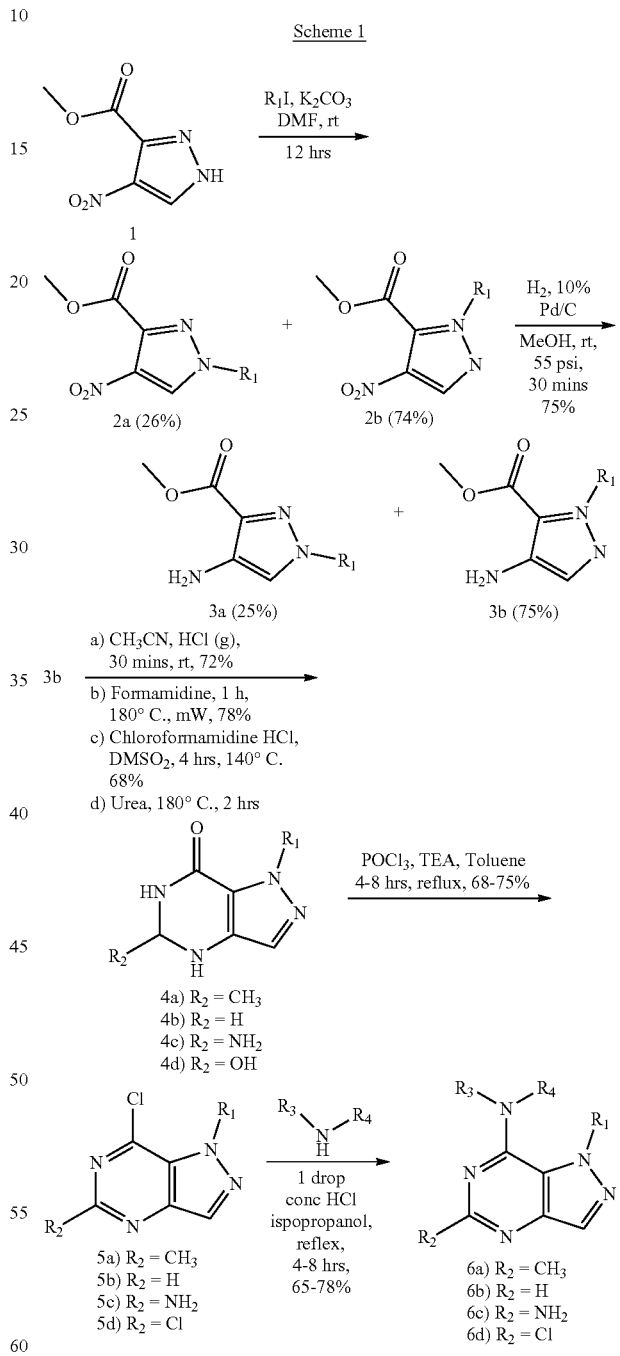

Scheme 1 a) CH$_3$CN, HCl (g), 30 mins, rt, 72%
b) Formamidine, 1 h, 180° C., mW, 78%
c) Chloroformamidine HCl, DMSO$_2$, 4 hrs, 140° C. 68%
d) Urea, 180° C., 2 hrs $R_1$ = alkyl $C_{1-6}$, $R_2$ = alkyl $C_{1-6}$, hydrogen, NR$^a$R$^b$, aryl, heteroaryl, halogen.
a, b = hydrogen, alkyl $C_{1-6}$
$R_3$ = hydrogen, $C_{1-6}$ alkyl, aryl, heteroaryl
$R_4$ = $C_{1-6}$ alkyl, substituted aryl, substituted heteroaryl General synthesis for substituted-N-methylanilines: According to Teichert et al.[17] substituted aniline (5-10 mmol) NaOMe (5 equiv) was added to a suspension of in MeOH (8-15 mL). The resulting solution was poured into a suspension of paraformaldehyde (1.4 equiv) in MeOH (5-10 mL). The reaction mixture was stirred for 5 hours at RT and then sodium borohydride (1 equiv) was added. The solution was heated to reflux for 2 h. After evaporating part of the solvent, the reaction mixture was treated with 1 M KOH. The product was extracted with diethyl ether, dried (anhydrous $Na_2SO_4$). Silica gel (3-5 g) was added followed by evaporation of the solvent under reduced pressure to afford a plug which was loaded on a silica column and eluted with Hexanes/EtOAc 2:1. The fractions containing the product spot (TLC) were pooled and evaporated under reduced pressure to afford substituted-N-methylanilines. General synthesis for alkyl 1-alkyl-4-nitro-1H-pyrazole-5-carboxylate (2a) and alkyll 1-alkyl-4-nitro-1H-pyrazole-3-carboxylate (2b): 4-nitro-1H-pyrazole-3-carboxylic acid ester (1) was alkylated with excess alkyl iodide in the presence of potassium carbonate in DMF. After flash chromatography on silica gel, two regioisomers, alkyl 1-alkyl-4-nitro-1H-pyrazole-3-carboxylate (2a, 1,3-isomer) and alkyl 1-alkyl-4-nitro-1H-pyrazole-5-carboxylate (2b, 1,5-isomer) were obtained in 26% and 74% yield, respectively. The structures of the isomers (2a, 2b) were determined by NOESY analysis: a NOESY correlation was observed between H-5 and alkyl protons in 2a. The nitro group of 2a and 2b was reduced by hydrogenation in the presence of a catalytic amount of 10% Pd/C to produce amines 3a and 3b, respectively. General procedure for synthesis of 4-6: The synthesis of target compounds 4 (Part II: Scheme I), commenced from cyclization of 3b with HCl (g) and acetonitrile, formamide, chloro-formamidine hydrochloride and urea to afford 4a-4d, respectively. Chlorination of 4a-4d with $POCl_3$ and TEA in toluene afforded 5a-5d in 68-75% yield. Treatment with appropriate substituted anilines in isopropanol with 1 drop of conc. HCl provided compounds 6a-6d of this invention (65-78% yields).

Synthesized Compounds: (6d1-6d9): See Table 2 for Complete Chemical Structure

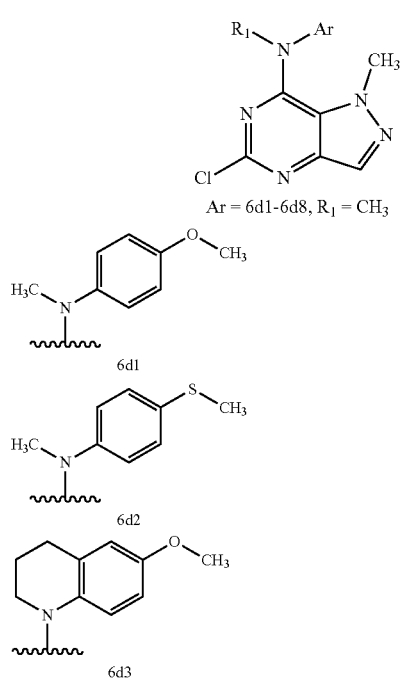

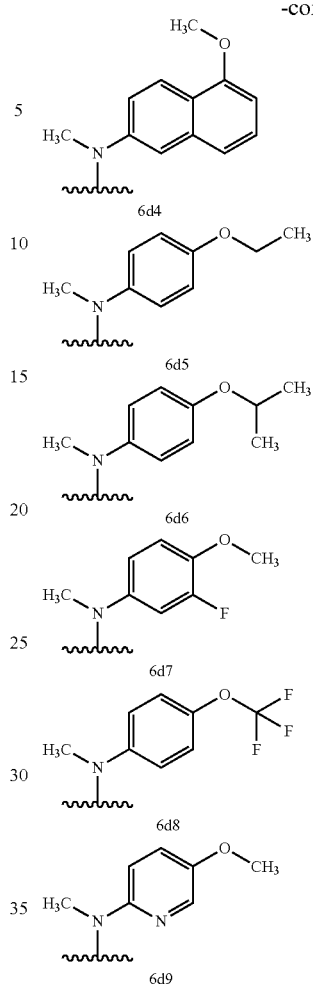

5,7-dichloro-1-methyl-1H-pyrazolo[4,3-d]pyrimidine (5d)

$^1$H NMR (400 MHz, DMSO-$d_6$) δ 7.48 (s, 1H), 3.95 (s, 3H)

5-chloro-N-(4-methoxyphenyl)-N,1-dimethyl-1H-pyrazolo[4,3-d]pyrimidin-7-amine (6d1)

$^1$H NMR (400 MHz, DMSO-$d_6$) δ 8.05 (s, 1H), 7.25 (d, J=8.9 Hz, 2H), 7.00 (d, J=8.9 Hz, 2H), 3.79 (s, 3H), 3.49 (s, 3H), 3.04 (s, 3H).

5-chloro-N,1-dimethyl-N-(4-(methylthio)phenyl)-1H-pyrazolo[4,3-d]pyrimidin-7-amine (6d2)

$^1$H NMR (400 MHz, DMSO-$d_6$) δ 8.09 (s, 1H), 7.31 (d, J=8.5 Hz, 2H), 7.24 (d, J=11.7 Hz, 2H), 3.35 (s, 3H), 3.09 (s, 3H), 2.49 (s, 3H).

1-(5-chloro-1-methyl-1H-pyrazolo[4,3-d]pyrimidin-7-yl)-6-methoxy-1,2,3,4-tetrahydroquinoline (6d3)

$^1$H NMR (400 MHz, DMSO-$d_6$) δ 8.12 (s, 1H), 6.93 (s, 1H), 6.74 (d, J=10.7 Hz, 2H), 4.08-3.82 (m, 2H), 3.75 (s, 3H), 3.21 (s, 3H), 2.91-2.74 (m, 1H), 2.17-1.94 (m, 2H).

5-chloro-N-(5-methoxynaphthalen-2-yl)-N,1-dimethyl-1H-pyrazolo[4,3-d]pyrimidin-7-amine (6d4)

$^1$H NMR (500 MHz, DMSO-$d_6$) δ 8.20 (d, J=9.0 Hz, 1H), 8.10 (s, 1H), 7.68 (d, J=2.3 Hz, 1H), 7.51 (dd, J=9.0, 2.3 Hz, 1H), 7.43 (t, J=7.9 Hz, 1H), 7.40-7.27 (m, 1H), 6.98 (dd, J=7.8, 0.9 Hz, 1H), 3.97 (s, 3H), 3.63 (s, 3H), 2.92 (s, 3H).

5-chloro-N-(4-ethoxyphenyl)-N,1-dimethyl-1H-pyrazolo[4,3-d]pyrimidin-7-amine (6d5)

$^1$H NMR (500 MHz, DMSO-$d_6$) δ 8.04 (s, 1H), 7.27-7.16 (m, 2H), 7.05-6.92 (m, 2H), 4.04 (q, J=7.0 Hz, 2H), 3.48 (s, 3H), 3.03 (s, 3H), 1.32 (t, J=6.9 Hz, 3H).

5-chloro-N-(4-isopropoxyphenyl)-N,1-dimethyl-1H-pyrazolo[4,3-d]pyrimidin-7-amine (6d6)

$^1$H NMR (500 MHz, DMSO-$d_6$) δ 8.05 (s, 1H), 7.21 (d, J=10.2 Hz, 2H), 6.98 (d, J=10.2 Hz, 2H), 4.76-4.51 (m, 1H), 3.48 (s, 3H), 3.05 (s, 3H), 1.27 (d, J=7.4 Hz, 6H).

5-chloro-N-(3-fluoro-4-methoxyphenyl)-N,1-dimethyl-1H-pyrazolo[4,3-d]pyrimidin-7-amine (6d7)

$^1$H NMR (400 MHz, DMSO-$d_6$) δ 6.94 (s, 1H), 6.48-6.32 (m, 1H), 6.26-6.16 (m, 1H), 6.02 (s, 1H), 3.70 (s, 3H), 3.38 (s, 3H), 2.61 (s, 3H).

5-chloro-N,1-dimethyl-N-(4-(trifluoromethoxy)phenyl)-1H-pyrazolo pyrimidin-7-amine (6d8)

$^1$H NMR (500 MHz, DMSO-$d_6$) δ 7.98 (s, 1H), 7.47 (d, J=9.0 Hz, 2H), 6.98 (d, J=9.0 Hz, 2H), 4.31 (s, 3H), 3.80 (s, 3H).

5-chloro-N-(4-methoxyphenyl)-1-methyl-1H-pyrazolo[4,3-d]pyrimidin-7-amine (6d9)

$^1$H NMR (500 MHz, DMSO-$d_6$) δ 7.59 (s, 1H), 7.28 (d, J=9.0 Hz, 2H), 6.82 (d, J=9.0 Hz, 2H), 3.95 (s, 3H), 3.31 (s, 3H).

TABLE 2 data MIA PaCa-2 cell lines and inhibition of colchicine binding

| Compounds | Compound activity in a P-gp overexpressing cell line[a] | | Inhibition of colchicine binding | | Inhibition of tubulin | |
|---|---|---|---|---|---|---|
| | OVCAR-8 IC$_{50}$ (nM) ± SD | NCI/ADR-RES IC$_{50}$ (nM) ± SD | 5 μM inhibitor % inhibition ± SD | 0.5 μM inhibitor % inhibition ± SD | assembly IC$_{50}$ (μM ± SD) | MIA PaCa-2 (nM ± SD) |
| Paclitaxel | 7.0 ± 2 | >5,000 | — | — | — | — |
| CS-A4 | 3.5 ± 0.7 | 2.3 ± 0.4 | 98 ± 0.1 | 80 ± 0.6 | 0.54 ± 0.06 | — |
| 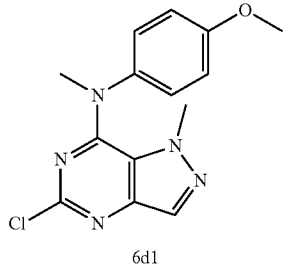 [SMILES: COc1ccc(N(C)c2nc(Cl)nc3cnn(C)c23)cc1] 6d1 | 9.0 ± 0.7 | 5.0 ± 0 | 94 ± 3 | 68 ± 3 | 0.45 ± 0.09 | 22.67 ± 1.128 |
| 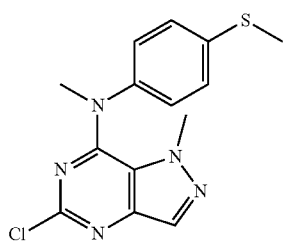 6d2 | 31 ± 2 | 17 ± 3 | 93 ± 0.5 | 64 ± 2 | 0.82 ± 0.02 | 20.92 ± 0.651 |
| 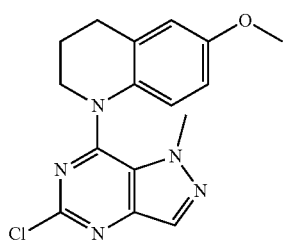 6d3 | 17 ± 2 | 8.0 ± 0.7 | 94 ± 0.4 | 68 ± 2 | 0.42 ± 0.07 | 47.97 ± 2.775 |

TABLE 2-continued data MIA PaCa-2 cell lines and inhibition of colchicine binding

| Compounds | Compound activity in a P-gp overexpressing cell line[a] | | Inhibition of colchicine binding | | Inhibition of tubulin | MIA PaCa-2 (nM ± SD) |
|---|---|---|---|---|---|---|
| | OVCAR-8 $IC_{50}$ (nM) ± SD | NCI/ADR-RES $IC_{50}$ (nM) ± SD | 5 μM inhibitor % inhibition ± SD | 0.5 μM inhibitor % inhibition ± SD | assembly $IC_{50}$ (μM ± SD) | |
| 6d4 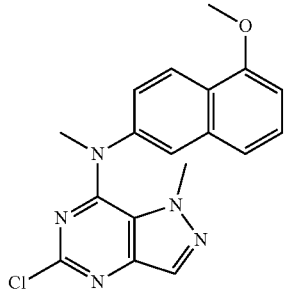 | 14 ± 3 | 11 ± 0.7 | 91 ± 1 | 66 ± 0.7 | 0.49 ± 0.01 | |
| 6d5 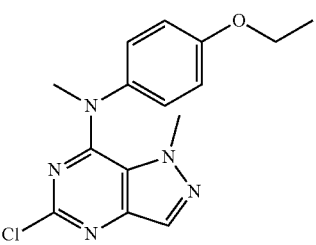 | 2.0 ± 1 | 4.0 ± 1 | 99 ± 0.4 | 88 ± 0.007 | 0.42 ± 0.07 | |
| 6d6 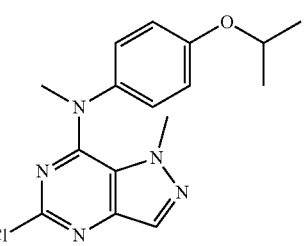 | 49.0 ± 10 | 44 ± 8.0 | 85 ± 1 | | 1.1 ± 0.08 | |
| 6d7 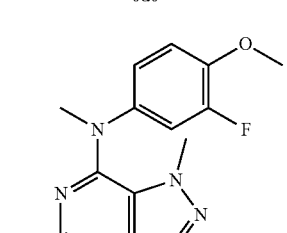 | 9.0 ± 1 | 7.0 ± 3 | 97 ± 0.3 | 77 ± 1 | 0.74 ± 0.04 | |
| 6d8 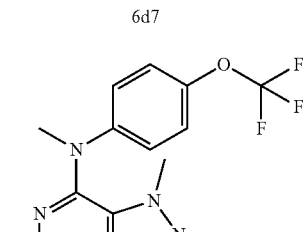 | 880 ± 40 | 730 ± 100 | 64 ± 5 | | 2.9 ± 0.2 | |

TABLE 2-continued data MIA PaCa-2 cell lines and inhibition of colchicine binding

| Compounds | Compound activity in a P-gp overexpressing cell line[a] | | Inhibition of colchicine binding | | Inhibition of tubulin assembly $IC_{50}$ (μM ± SD) | MIA PaCa-2 (nM ± SD) |
|---|---|---|---|---|---|---|
| | OVCAR-8 $IC_{50}$ (nM) ± SD | NCI/ADR-RES $IC_{50}$ (nM) ± SD | 5 μM inhibitor % inhibition ± SD | 0.5 μM inhibitor % inhibition ± SD | | |
| 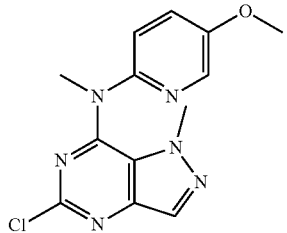 6d9 | 200 ± 40 | 150 ± 0 | 74 ± 2 | | 1.2 ± 0.2 | |
| GEM | — | — | — | — | — | 296.8 ± 60.4 |
| PMX | — | — | — | — | — | 16.1 ± 1.4 |

TABLE 3

| Agent | MCF-7 WT $EC_{50}$ (nM) | MCF-7-TUBB3 β3-tubulin $EC_{50}$ (nM) | RESISTANCE RATIO β3-tubulin/WT | MCF-7/TAX Pgp $EC_{50}$ (nM) | RESISTANCE RATIO Pgp/WT |
|---|---|---|---|---|---|
| 6d1 | 2.0 ± 0.3 | 3.3 ± 0.4 | 1.1 | 15.1 ± 2.0 | 3.8 |
| 6d4 | 35.2 ± 4.7 | 16.8 ± 1.5 | 0.5 | 43.0 ± 7.2 | 1.2 |
| 6d5 | 7.7 ± 0.7 | 9.7 ± 1.0 | 1.3 | 31.3 ± 3.5 | 4.0 |
| 6d7 | 1.7 ± 0.2 | 2.6 ± 0.4 | 1.6 | 8.1 ± 0.2 | 4.8 |
| PACLITAXEL | 194.2 | 2065.8 | 10.6 | 3225.0 | 16.6 |

REFERENCES

1. Jordan, M. A.; Wilson, L. Microtubules as a Target for Anticancer Drugs. *Nat. Rev. Cancer* 2004, 4, 253-265.
2. Dumontet, C; Jordan, M. A. Microtubule-binding agents: A Dynamic Field of Cancer Therapeutics. *Nat. Rev. Drug Discov.* 2010, 9, 790-803.
3. Prota, A. E.; Bargsten, K.; Northcote P. T.; Marsh M.; Altmann K. H.; Miller J. H.; Diaz J. F.; Steinmetz M. O. Structural Basis of Microtubule Stabilization by Laulimalide and Peloruside A. *Angew. Chem. Int. Ed.* 2014, 53, 1621-1625
4. Prota, A. E.; Bargsten, K.; Diaz J. F.; Marsh M.; Cuevas C.; Liniger, M.; Neuhaus, C.; Andreu, J. M.; Altmann K. H.; Miller J. H.; Steinmetz M. O. A new tubulin binding site and pharmacophore for microtubule-destabilizing anticancer drugs. *Proc. Natl. Acad. Sci. U.* 2014, 111, 13817-13821
5. Carlson, R. O. New Tubulin Targeting Agents Currently in Clinical Development *Expert Opin. Investig. Drugs* 2008, 17, 707-722.
6. Kavallaris, M. Microtubules and resistance to tubulin-binding agents. *Nat. Rev. Cancer,* 2010, 3, 194-204.
7. Ling, V. Multidrug Resistance: Molecular Mechanisms and Clinical Relevance. *Cancer Chemother.* 1997, 40, S3-8.
8. Chiou, J. F.; Liang, J. A.; Hsu, W. H.; Wang, J. J.; Ho, S. T.; Kao, A. Comparing the Relationship of Taxol-based Chemotherpay Response with P-glycoprotein and Lung Resistance-related Protein Expression in Non-Small Cell Lung Cancer. *Lung* 2003, 181, 267-273.
9. Seve, P.; Isaac, S.; Tredan, O.; Souquet, P.-J.; Pacheco, Y.; Perol, M.; Lafanechere, L.; Penet, A.; Peiller, E.-L.; Dumontet, C. Expression of Class III β-Tubulin Is Predictive of Patient Outcome in Patients with Non-Small Cell Lung Cancer Receiving Vinorelbine-Based Chemotherapy. *Clin. Cancer Res.* 2005, 11, 5481-5486.
10. Tommasi, S.; Mangia, A.; Lacalamita, R.; Bellizzi, A.; Fedele, V.; Chiriatti, A.; Thomssen, C.; Kendzierski, N.; Latorre, A.; Lorusso, V.; Schittulli, F.; Zito, F.; Kavallaris, M.; Paradiso, A. Cytoskeleton and Paclitaxel Sensitivity In Breast Cancer: The Role Of Beta-Tubulins. *Int. J. Cancer* 2007, 120, 2078-2085.
11. Ferrandina, G.; Zannoni, G. F.; Martinelli, E.; Paglia, A.; Gallotta, V.; Mozzetti, S.; Scambia, G.; Ferlini, C. Class III β-Tubulin Overexpression is a Marker of Poor Clinical Outcome in Advanced Ovarian Cancer Patients. *Clin. Cancer Res.* 2006, 12, 2774-2779.
12. Stengel, C; Newman, S. P.; Lesse, M. P.; Potter, B. V. L.; Reed, M. J.; Purohit, A. Class III Beta-Tubulin Expression and in vitro Resistance To Microtubule Targeting Agents. *Br. J. Cancer* 2010, 102, 316-324.
13. a) Gangjee, A.; Pavana, R. K.; Li, W.; Hamel, E.; Westbrook, C.; Mooberry S. L. Novel Water-Soluble Substituted Pyrrolo[3,2-d]pyrimidines: Design, Synthesis and Biological Evaluation as Antitubulin Antitumor Agents. *Pharm. Res.* 2012, 29, 3033-3039; b) Gangjee, A., Shah, K., Hargreaves, N. D., Mooberry, S. L. and Ihnat, M. Design and biological evaluation of substituted pyrrolo[3,2-d]pyrimidines as dual acting RTK and microtubule targeting agents. 107th AACR Annual Meeting: 2016, New Orleans, La., Apr. 16-20, 2016

14. Andrea E. Prota, Franck Danel, Felix Bachmann, Katja Bargsten, . . . Michel O. Steinmetz. The Novel Microtubule-Destabilizing Drug BAL27862 Binds to the Colchicine Site of Tubulin with Distinct Effects on Microtubule Organization. *J. Mol. Biol.* 2014, 426, 1848-1860
15. Biologics Suite 2018-2, Schrödinger, LLC, New York, N.Y., 2018.
16. Regiec, A., Mastalarz., H., Mastalarz., A. and Kochel, A. Methylation of 4-nitro-3(5)-pyrazolecarboxylic acid. *Tetrahedron Lett.* 2009, 50, 2624-2627.
17. Teichert, A; Jantos, K.; Harms, K; Studer, A. One-pot hemolytic aromatic substitutions/HWE olefinations under microwave conditions for the formation of a small oxindole library. *Org. Lett.* 2004, 6, 3477-3480.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of treating a patient having cancer comprising administering to said patient a therapeutically effective amount of a compound of Formula I, or optionally a salt or a hydrate of said compound of Formula I:

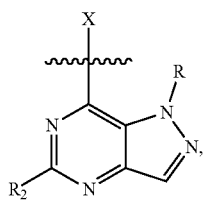

wherein X is selected from the group consisting of:

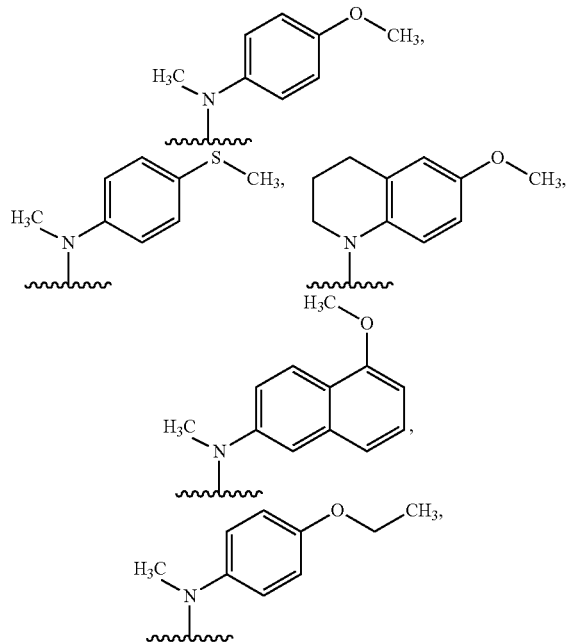

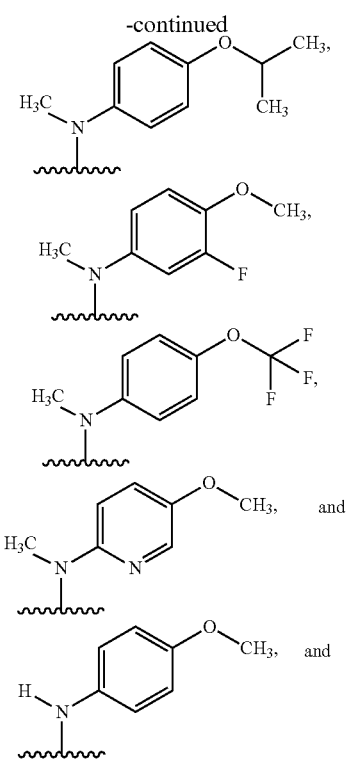

wherein R is an alkyl group having from one to ten carbon atoms, and wherein $R_2$ is a halogen atom.

2. The method of claim 1 including wherein said compound of Formula I includes wherein R is a methyl group.

3. The method of claim 1 including wherein said compound of Formula I includes wherein $R_2$ is said halogen atom that is a chlorine.

4. The method of claim 2 including wherein said compound of Formula 1 wherein $R_2$ is said halogen atom that is a chlorine.

5. A method of treating a patient having cancer comprising administering to said patient a therapeutically effective amount of a pharmaceutical composition comprising a compound of Formula I, or optionally a salt or a hydrate of said compound of Formula I:

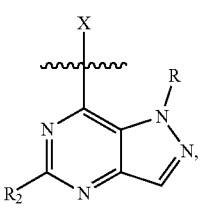

wherein X is selected from the group consisting of:

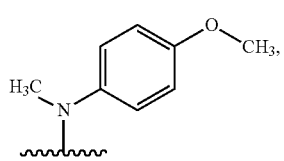

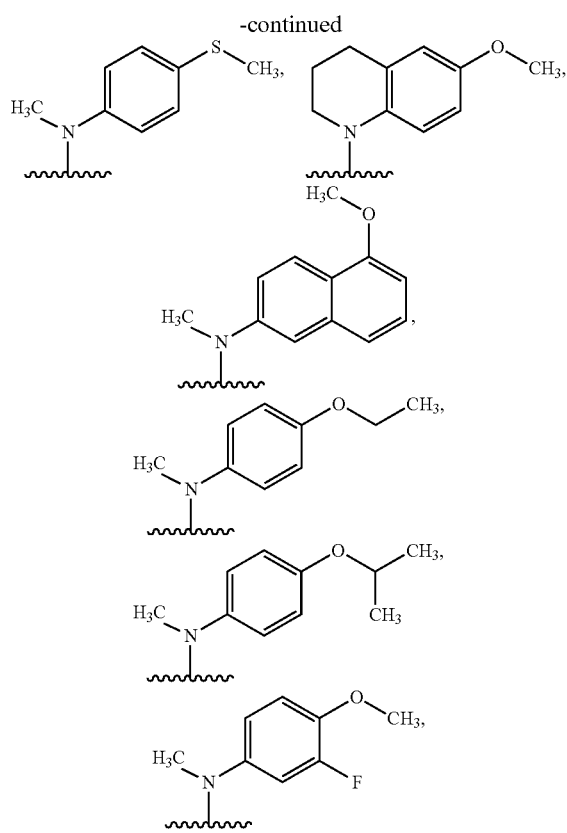

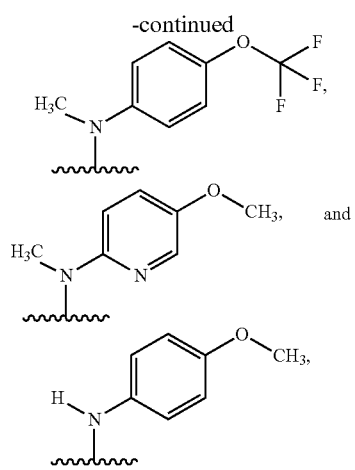

wherein R is an alkyl group having from one to ten carbon atoms, and wherein $R_2$ is a halogen atom.

6. The method of claim 5 including wherein said compound of Formula I includes wherein R is a methyl group.

7. The method of claim 5 including wherein said compound of Formula I wherein $R_2$ is said halogen that is a chlorine.

8. The method of claim 6 including wherein said halogen is a chlorine.

9. The method of claim 5 including wherein said pharmaceutical composition includes a pharmaceutically acceptable carrier.

* * * * *